(12) United States Patent
Yamakita et al.

(10) Patent No.: US 6,293,910 B1
(45) Date of Patent: *Sep. 25, 2001

(54) ENDOSCOPE, METHOD OF MANUFACTURING THE SAME, AND INSERTION MEMBER

(75) Inventors: Hiroyuki Yamakita, Osaka; Hiroshi Atsuta, Katano; Shinji Uchida, Neyagawa; Kiyoko Oshima, Shijonawate, all of (JP)

(73) Assignee: Matsushita Electric Industrial Co., Ltd., Osaka (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/171,080
(22) PCT Filed: Feb. 12, 1998
(86) PCT No.: PCT/JP98/00558
  § 371 Date: Oct. 13, 1998
  § 102(e) Date: Oct. 13, 1998
(87) PCT Pub. No.: WO98/35607
  PCT Pub. Date: Aug. 20, 1998

(30) Foreign Application Priority Data

Feb. 13, 1997 (JP) .................................................. 9-028614
Feb. 26, 1997 (JP) .................................................. 9-041911
Jun. 9, 1997 (JP) .................................................. 9-151290

(51) Int. Cl.$^7$ .................................................. A61B 1/07
(52) U.S. Cl. .................... 600/132; 600/110; 600/177; 600/182
(58) Field of Search .................................... 600/109, 110, 600/111, 112, 114, 131, 132, 138, 160, 172, 178, 182, 177; 385/117, 902

(56) References Cited

U.S. PATENT DOCUMENTS 4,491,865 * 1/1985 Danna et al. ......................... 600/110
4,777,524 * 10/1988 Nakajima et al. .................... 348/76

(List continued on next page.)

FOREIGN PATENT DOCUMENTS 2-503361   10/1990   (JP) .
3-502741    6/1991   (JP) .

(List continued on next page.)

OTHER PUBLICATIONS

Search Report corresponding to application No. PCT/JP98/00558 dated Apr. 14, 1998.
English translation of Form PCT/ISA/210.
European Search Report dated Apr. 12, 2000, application No. 98902192.

* cited by examiner

*Primary Examiner*—John P. Leubecker
(74) *Attorney, Agent, or Firm*—Ratner & Prestia

(57) ABSTRACT

An endoscope has an elongated insertion portion to be inserted into a subject,
  wherein the insertion portion directs illumination light for illuminating the subject, and comprises a cylindrical light directing member being hard enough to maintain its configuration, and an optical system and an image sensing device provided inside the light directing member for observing the subject, and
  wherein the image sensing device comprises a solid-state image sensing device for converting light from the optical system into an electric signal, and a circuit board electrically connected to the solid-state image sensing device.

25 Claims, 22 Drawing Sheets

U.S. PATENT DOCUMENTS

| | | | |
|---|---|---|---|
| 4,788,967 | * 12/1988 | Ueda | 600/129 |
| 4,790,295 | * 12/1988 | Tashiro | 600/176 |
| 4,819,620 | * 4/1989 | Okutsu | 600/114 |
| 4,979,498 | * 12/1990 | Oneda et al. | 600/121 |
| 5,051,824 | * 9/1991 | Nishigaki | 348/68 |
| 5,184,602 | * 2/1993 | Anapliotis et al. | 600/137 |
| 5,213,092 | 5/1993 | Uram . | |
| 5,239,983 | * 8/1993 | Katsurada | 600/178 |
| 5,379,756 | * 1/1995 | Pileski et al. | 600/109 |
| 5,419,313 | 5/1995 | Lemke . | |
| 5,432,876 | * 7/1995 | Appeldorn et al. | 385/31 |
| 5,522,006 | * 5/1996 | Takeuchi et al. | 385/139 |
| 5,569,161 | * 10/1996 | Ebling et al. | 600/121 |
| 5,588,949 | * 12/1996 | Taylor et al. | 600/176 |
| 5,617,498 | * 4/1997 | Cawood | 385/117 |
| 5,868,664 | * 2/1999 | Speier et al. | 600/112 |
| 5,879,285 | * 3/1999 | Ishii | 600/110 |
| 5,961,445 | * 11/1999 | Chikama | 600/112 |
| 5,986,693 | * 11/1999 | Adair et al. | 348/76 |

FOREIGN PATENT DOCUMENTS

| | | |
|---|---|---|
| 4-176436 | 6/1992 | (JP) . |
| 6-175041 | 6/1994 | (JP) . |
| 6-254049 | 9/1994 | (JP) . |
| 7-5376 | 1/1995 | (JP) . |
| 7-327923 | 12/1995 | (JP) . |
| 8-122663 | 5/1996 | (JP) . |
| 8-262338 | 10/1996 | (JP) . |
| WO94/09694 | 5/1994 | (WO) . |
| WO95/00066 | 1/1995 | (WO) . |

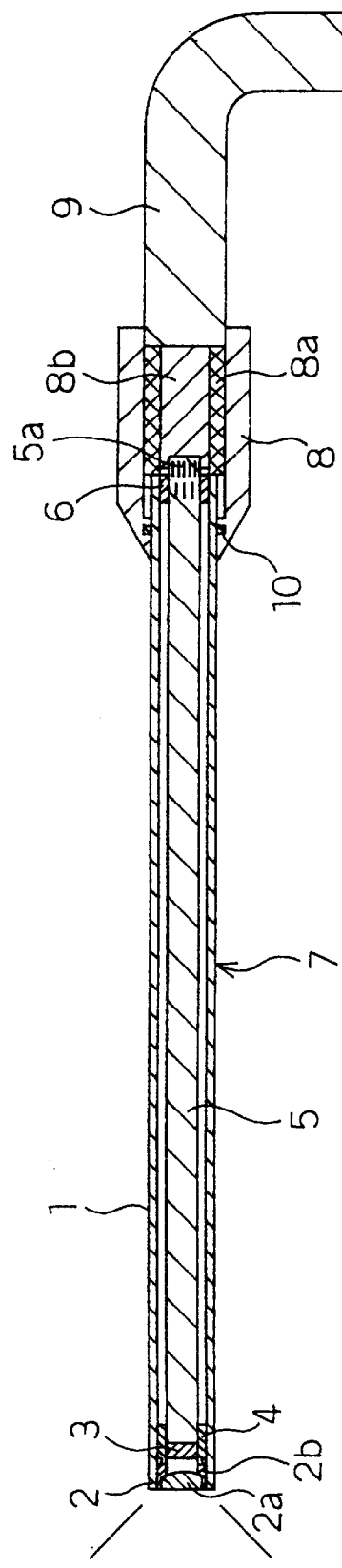
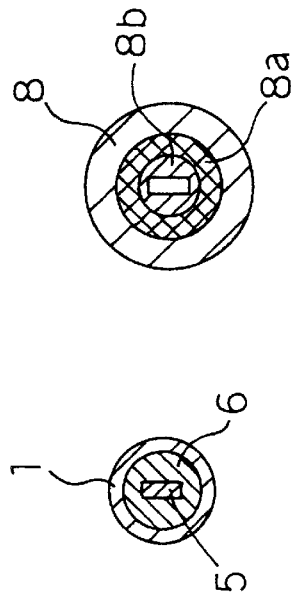
Fig. 1(A) Fig. 1(B) Fig. 1(C)

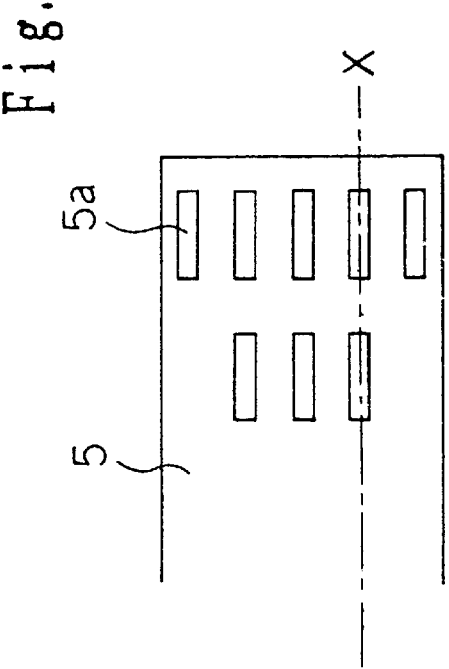
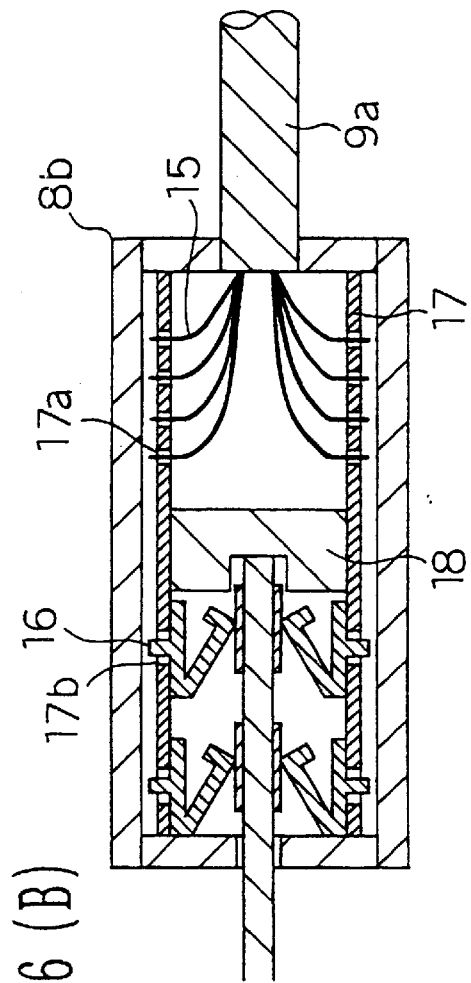
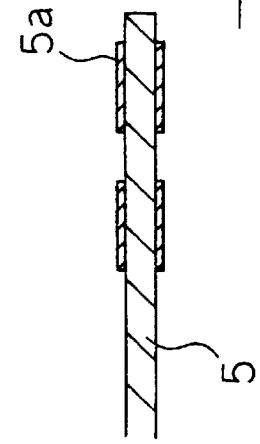
Fig. 6 (A)
Fig. 6 (B)

Fig. 7(A)
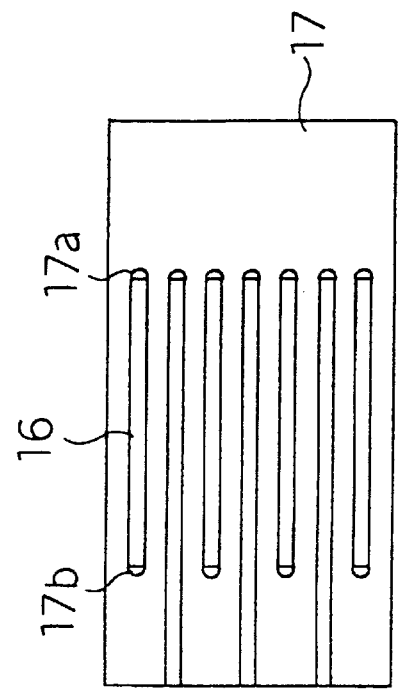
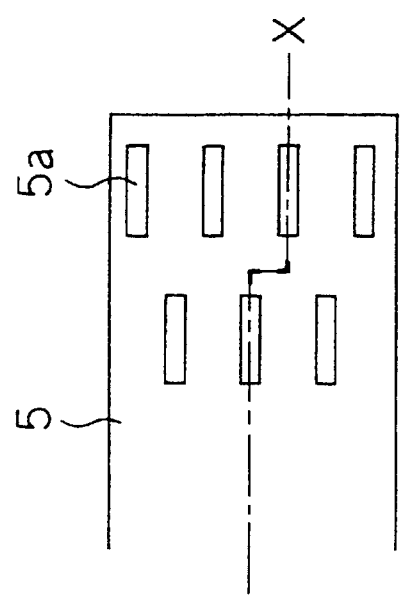
Fig. 7(B)
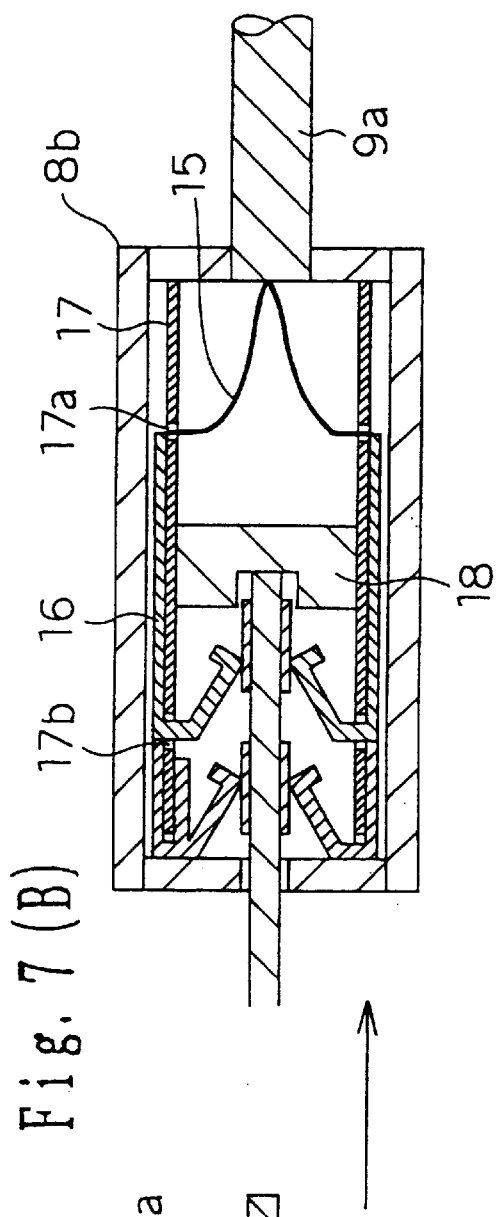
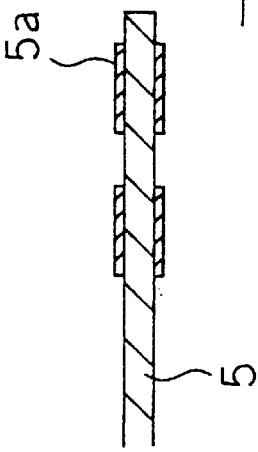

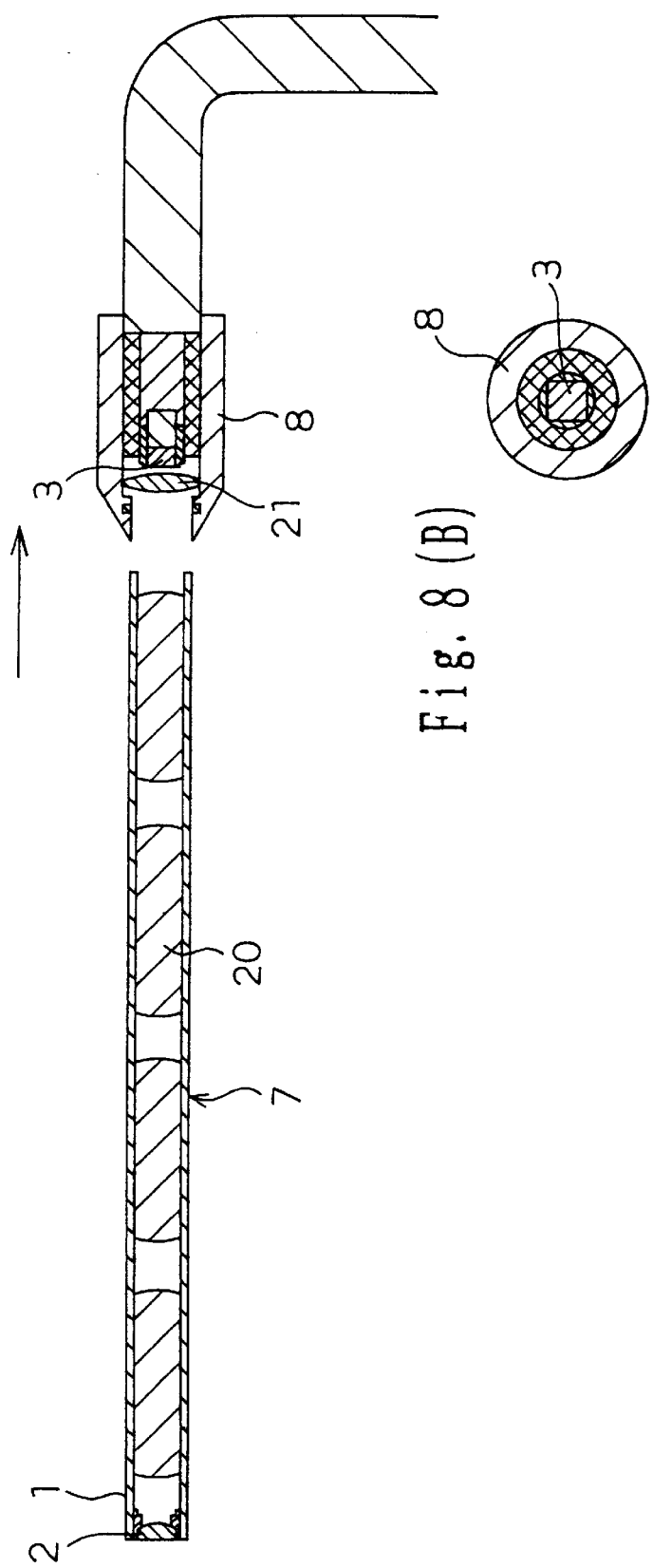

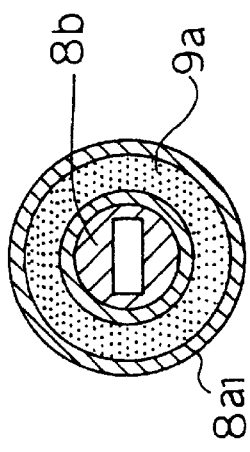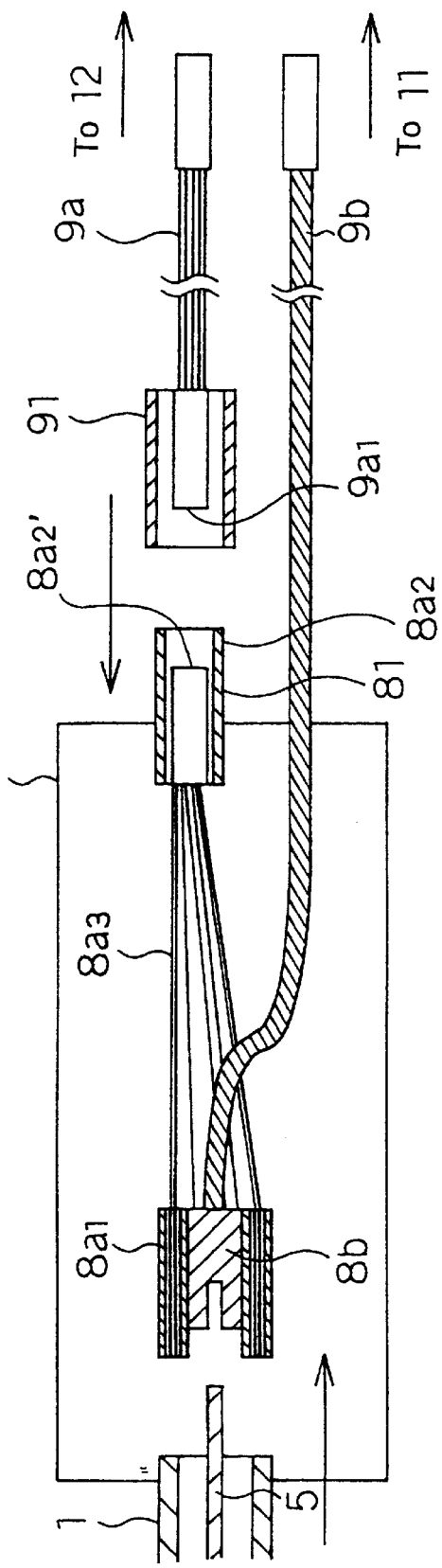
Fig. 10 (A)
Fig. 10 (B)

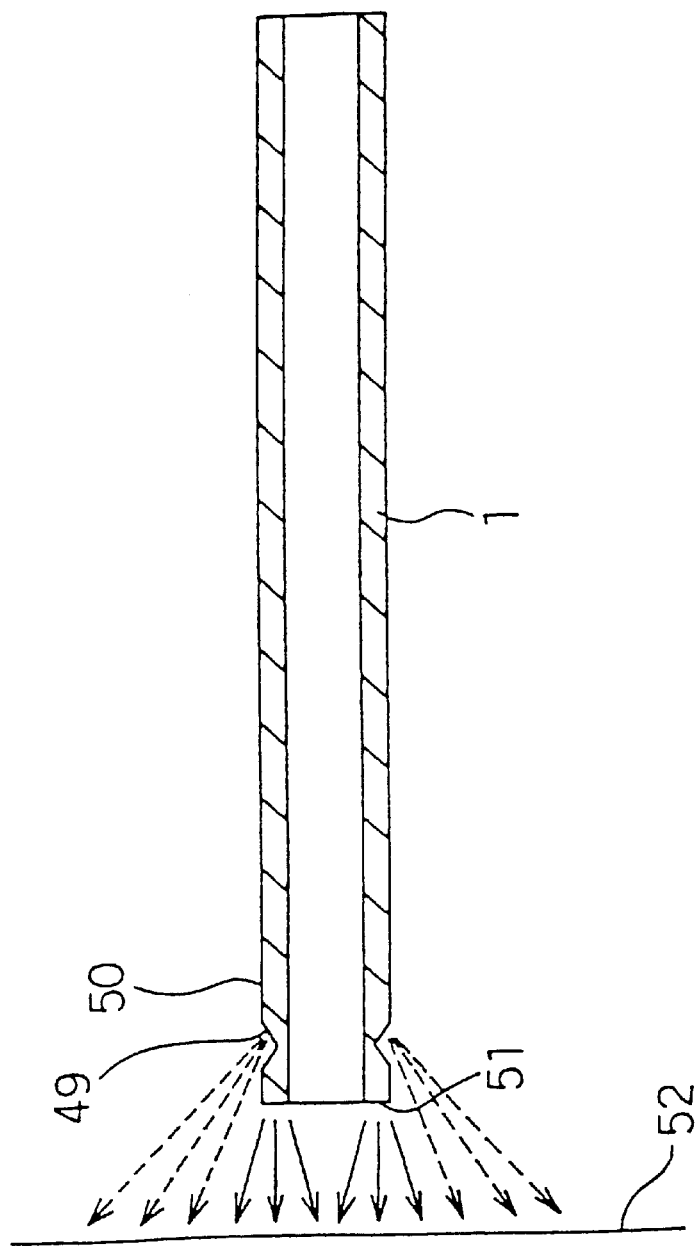

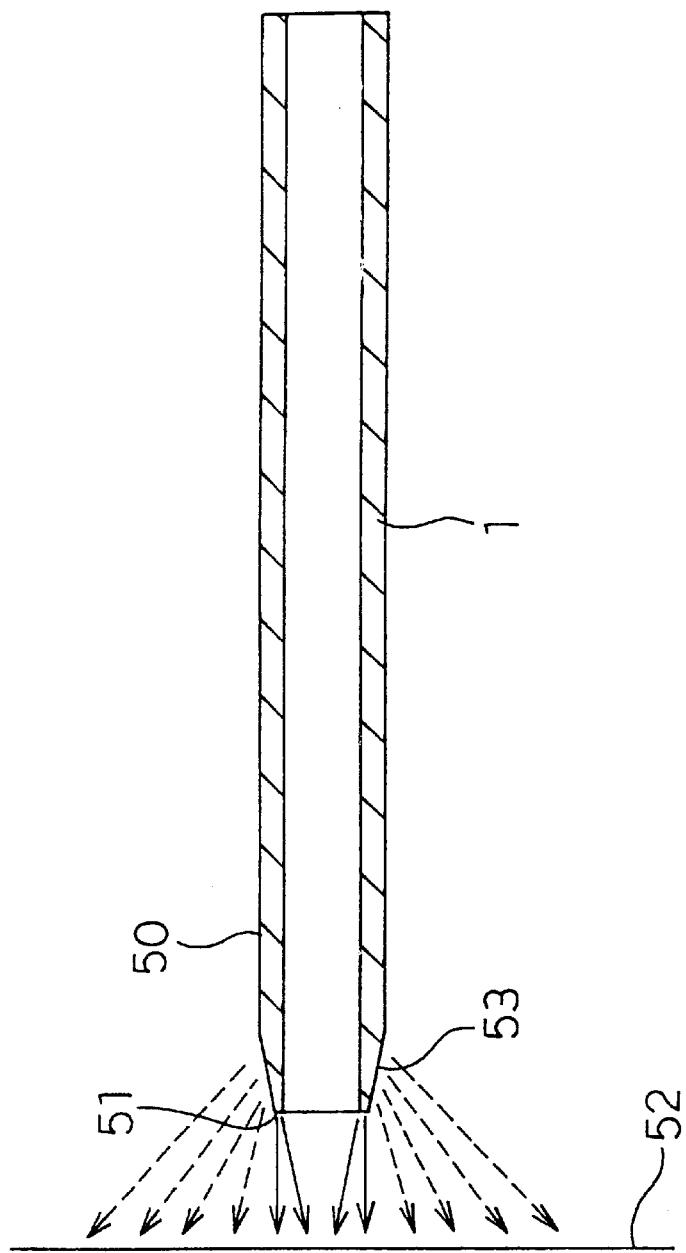

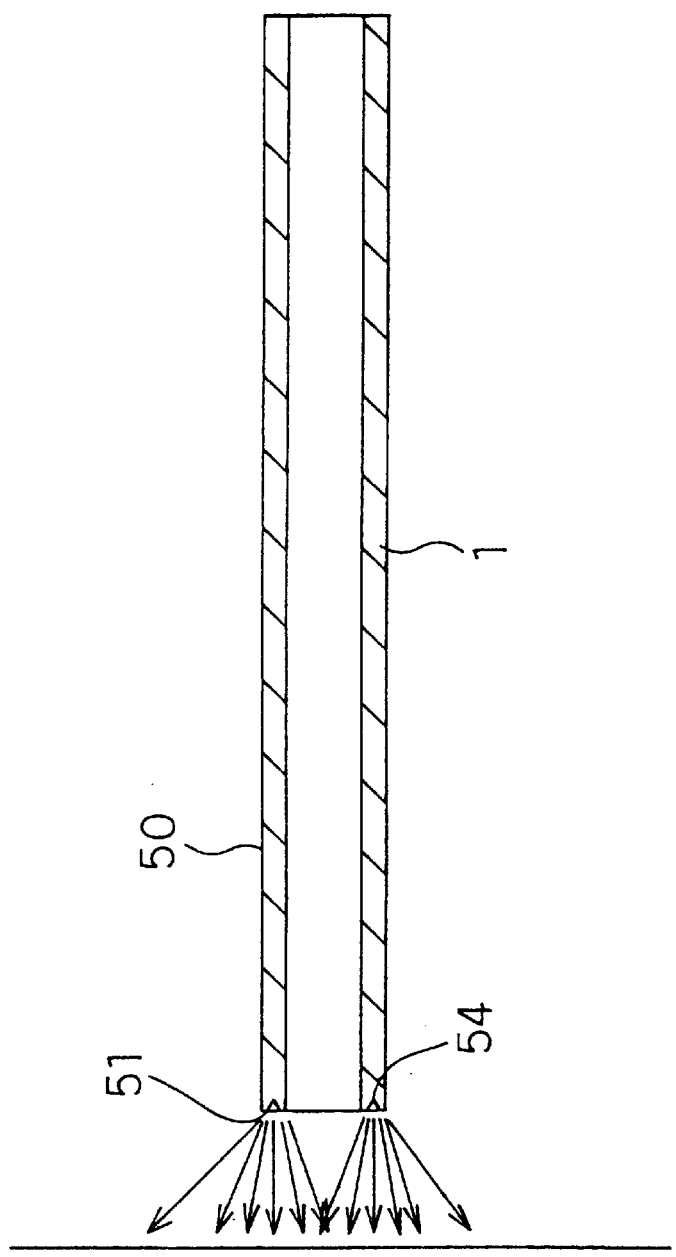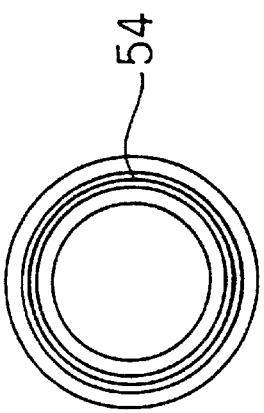
Fig. 19(A)
Fig. 19(B)

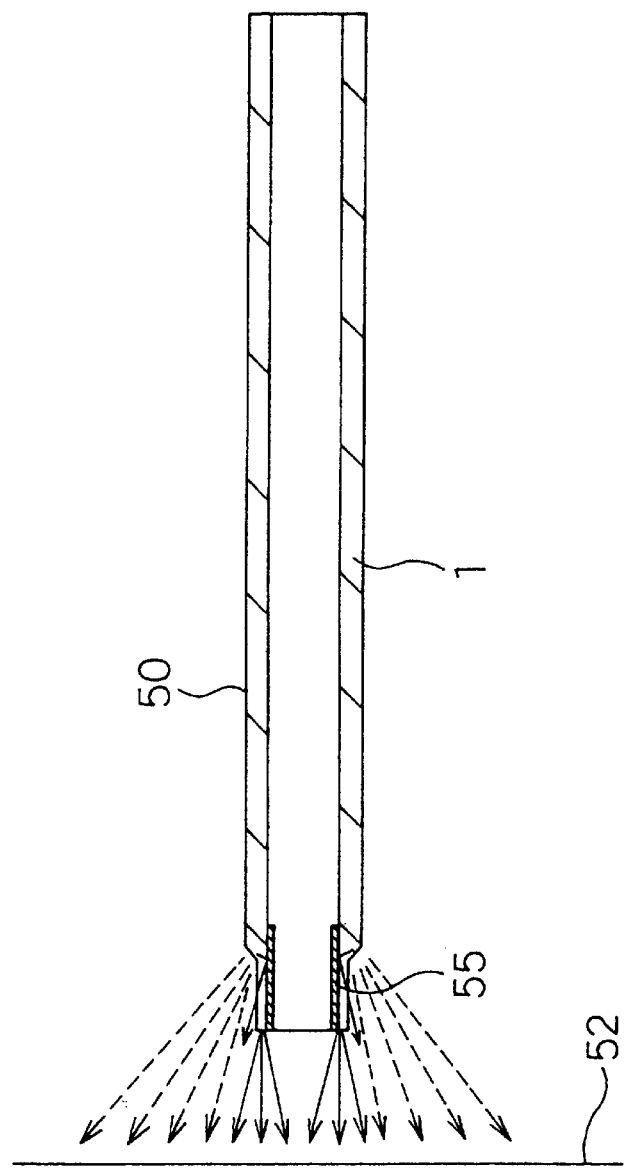
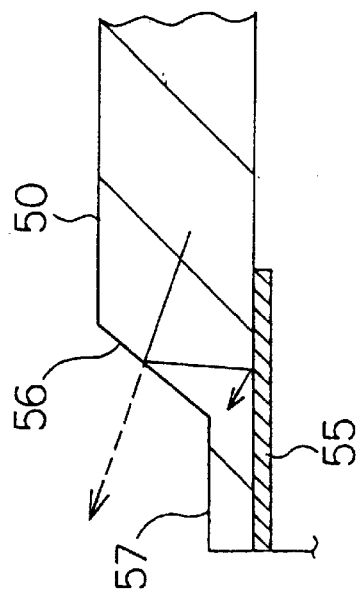
Fig. 20 (A)
Fig. 20 (B)

ENDOSCOPE, METHOD OF MANUFACTURING THE SAME, AND INSERTION MEMBER

FIELD OF THE INVENTION

The present invention relates to an endoscope used as a medical endoscope or an industrial endoscope and so on, and a method of manufacturing the same.

BACKGROUND ART

In recent years, surgical instruments of disposable type being thrown away after one use without being washed for reuse have become widespread for reasons such as the problem of infection and the troublesome washing and disinfection. As for the endoscope, there is a demand for a low-priced disposable type.

To meet this demand, a disposable endoscope has been proposed which can be inexpensively manufactured because of the insertion portion employing a structure in which an imaging optical system for forming a subject image and an illumination optical system for illuminating the subject are integrated by use of resin.

Moreover, an optical inspection tube has been proposed which is suitable for use as a disposable endoscope because an optical pipe made of a polymeric material such as acrylic is used as a light guide and a similar polymeric material is used as the material of other structural elements such as the objective lens and the relay lens.

An example of the above-mentioned endoscope will hereinafter be described with reference to the drawings.

FIG. 15(A) is a cross-sectional view of an insertion portion of an endoscope shown in Japanese Laid-open Patent Application No. H6-254049. FIG. 15(B) is a general structural view of the endoscope.

As shown in FIG. 15(B), an endoscope 101 is an electronic endoscope having a CCD 117 at its front end portion, and has an insertion portion 102 to be inserted in the observation portion of the subject. The insertion portion 102 is connected through a cable 125 to a light source apparatus 130 for supplying illumination light to the insertion portion 102 and to a CCU 129 for processing image sensing signals from the CCD 117. The insertion portion 102 and the cable 125 are electrically connected by engaging male pins 121 of an video connector 120 with female pins of a corresponding video connector 120 of the connector 107 of the cable 125. The insertion portion 102 is formed, as shown in FIG. 15(A), by integrating by use of a resin 108 an illumination optical system comprising a light guide 112 for transmitting the illumination light and an illumination lens 118, an observation optical system comprising a plurality of objective lenses 113 and 114, the CCD 117 and a signal line 123. Since the insertion portion 102 is inexpensively manufactured because of this structure, it can be thrown away after one use.

FIG. 16(A) is a side cross-sectional view of an endoscope shown in Japanese Patent Kohyo No. H2-503361. FIG. 16(B) is an exploded perspective view of the endoscope and shows a series of rod lenses placed from one end to the other inside a molded optical pipe. FIG. 16(C) is a cross-sectional view showing in detail the position of one of the rod lenses placed inside the optical pipe.

As shown in FIG. 16, an optical inspection apparatus 210 is an optical inspection tube for an inspector 212 to inspect an area 224 in a body cavity, and has inside an elongated optical pipe 214 for directing light from a light source 220. The optical pipe 214 has an elongated portion extending from a distal end 218 of the pipe to a bending portion in the vicinity of a proximal end 216 of the pipe, and has an elongated cradle-shaped concave portion 254 inside the elongated portion. The lens units such as relay lens units 238 are first fixed in the concave portion 254 of the optical pipe 214 and then inserted into a pipe 258 made of aluminum. Then, their centers are aligned with each other and the insertion portion is completed. By using ones molded from a polymeric material such as acrylic as structural elements such as the optical pipe 214, objective lens units 222 and the relay lens units 238, a structure suitable for use as a disposable endoscope is achieved.

However, the endoscope having the above-described structure has the following problems:

(1) Since the light guides 112 and 214 for transmitting the illumination light are provided separately from the exterior structures 108 and 258 of the insertion portions 102 and 210, the cost increases and the assembly process is complicated.

(2) In the case of a disposable endoscope, if a material which cannot be incinerated such as a metal and glass is used for the exterior structure of the insertion portion and the light guide, medical waste increases.

(3) When an electric connection portion for transmitting video signals and a light directing cable connection portion for transmitting the illumination light are separately provided and taken out from different directions, it is necessary for the light directing member to have a bending configuration, so that the assembly and the connection are complicated. In addition, the configuration of the operation portion of the endoscope is complicated, so that easy operation cannot be achieved.

(4) Since the CCD is aligned with the objective lens and inserted into the insertion portion of the endoscope under a condition where the CCD is connected to the signal line, handling is not easy and the assembly process is complicated.

Since the pin-shaped connector conventionally used as the electric connection portion for transmitting video signals has a structure unsuitable for enabling easy connection and disconnection and it is necessary to provide a connector also on the side of the insertion portion, the price increases.

(5) Since parts which require positioning and fixing such as the objective optical system, the imaging optical system and the image sensing optical system are necessarily positioned and fixed in advance with screws before inserted into the insertion portion of the endoscope, and a dedicated mounting member and drilling of holes for fixing are necessary, the structure of the insertion portion is intricate and the assembly process is complicated.

FIG. 21 is a structural view of an insertion portion of an endoscope proposed in Japanese Laid-open Patent Application No. H8-122663.

This endoscope comprises a light guide 61 formed of a silica optical fiber bundle for transmitting the illumination light, a light diffusing device 62 for diffusing the illumination light having exited from an end surface 61a of the light guide 61 and an image sensing optical system 63 for image-sensing reflected light from the subject.

The light diffusing device 62 is used for distributing the intensity of the illumination light for illuminating the subject so as to have desired characteristics. Examples of the conventional light diffusing device 62 include a concave lens using a grinding technology, a hologram lens using a holography technology, and an LSD (light shaping diffuser) optical device using a refraction effect of light and manufactured and marketed by POC (Physical Optics Corporation) of the United States.

By using the light diffusing device 62, it has been attempted to improve the illumination distribution such that the central portion of the sensed area is bright and the peripheral portion thereof is dark.

However, the endoscope using the light diffusing device as described above has the following problems:

(6) Since the concave lens requires grinding, the cost is extremely high.

(7) Since the hologram lens diffuses the illumination light by use of a diffraction phenomenon of light, the color reproducibility is inferior, so that nonuniformity is caused in color.

(8) In the case of the one comprising the LSD, although the nonuniformity in color is not caused, the cost increases because it is necessary to dispose it as a separate member in the vicinity of an end surface of the light guide so as to be exclusively used for that purpose.

(9) Since only the light having exited from an end surface of the optical fiber bundle is diffused, the diffusion effect is limited, so that it is difficult to obtain a desired illumination distribution.

DISCLOSURE OF THE INVENTION

Thus, the conventional endoscope has the above-mentioned problems (1) to (9).

An object of the present invention is to solve the above-mentioned problems (1) to (9) of the prior art.

An endoscope of the present invention comprises an elongated insertion portion to be inserted into a subject, wherein said insertion portion directs illumination light for illuminating said subject, and comprises a cylindrical light directing member being hard enough to maintain its configuration, and an optical system and an image sensing device provided inside said light directing member for observing said subject, and wherein said image sensing device comprises a solid-state image sensing device for converting light from said optical system into an electric signal, and a circuit board electrically connected to said solid-state image sensing device.

An method of manufacturing an endoscope of the present invention is that in which an elongated insertion portion to be inserted into a subject directs illumination light for illuminating said subject, and comprises a cylindrical light directing member being hard enough to maintain its configuration, and an optical system and an image sensing device provided inside said light directing member for observing said subject, and in which said image sensing device comprises a solid-state image sensing device for converting light from said optical system into an electric signal and a circuit board electrically connected to said solid-state image sensing device, wherein said optical system and said image sensing device, or said image sensing device is inserted and fixed in said light directing member.

In another aspect, method of manufacturing an endoscope of the present invention is that in which an elongated insertion portion to be inserted into a subject directs illumination light for illuminating said subject, and comprises a cylindrical light directing member being hard enough to maintain its configuration, and an optical system and an image sensing device provided inside said light directing member for observing said subject, in which said image sensing device comprises a solid-state image sensing device for converting light from said optical system into an electric signal and a circuit board electrically connected to said solid-state image sensing device, in which said circuit board is formed to extend from said solid-state image sensing device to a rear end portion of said light directing member, and in which electrode portions for disconnectable electrical connection with a signal cable are formed at a rear end portion of said circuit board, wherein position adjustment of said optical system previously fixed to said front end portion of said light directing member, and said solid-state image sensing device is made by operating said rear end portion of said circuit board.

In a further aspect, a method of manufacturing an endoscope of the present invention is that in which an elongated insertion portion to be inserted into a subject directs illumination light for illuminating said subject, and comprises a cylindrical light directing member being hard enough to maintain its configuration, and an optical system, or an optical system and an image sensing device, provided inside said light directing member for observing said subject, wherein a photo-setting resin is used as fixing means for fixing said optical system or said image sensing device to said light directing member.

An endoscope of the present invention comprises an elongated insertion portion to be inserted into a subject, wherein said insertion portion comprises a light directing member of hollow cross section for directing illumination light for illuminating said subject, and an optical system and an image sensing device provided inside said light directing member for observing said subject, and wherein a light dispersing portion having a configuration different from a configuration of other portion of said light directing member and a function of dispersing said illumination light is formed at a front end portion of said light directing member.

An insertion member of the present invention constitutes an endoscope for observing a subject, and to be inserted into said subject, wherein said insertion member comprises: a cylindrical light directing member for directing illumination light for illuminating said subject, and being hard enough to maintain its configuration; and a light transmission system disposed inside said light directing member for transmitting light from said subject.

BRIEF DESCRIPTION OF THE DRAWINGS

FIG. 1 is a cross-sectional view showing the structure of an endoscope according to a first embodiment of the present invention;

FIG. 6 is a cross-sectional view showing the structure of a signal connection portion of the endoscope according to the first embodiment of the present invention;

FIG. 7 is a cross-sectional view showing the structure of an signal connection portion of the endoscope according to the first embodiment of the present invention;

FIG. 8 is a cross-sectional view showing the structure of an endoscope according to a second embodiment of the present invention;

FIG. 10 is a cross-sectional view showing a connector-centered structure of an endoscope according to a fourth embodiment of the present invention;

FIG. 17a is an enlarged cross-sectional view of a front end portion of a light directing member of an endoscope according to an eighth embodiment of the present invention showing a concentrical groove;

FIG. 18 is an enlarged cross-sectional view of a front end portion of a light directing member of an endoscope according to a ninth embodiment of the present invention;

FIG. 19 is an enlarged cross-sectional view of a front end portion of a light directing member of an endoscope according to a tenth embodiment of the present invention;

FIG. 20 is an enlarged cross-sectional view of a front end portion of a light directing member of an endoscope according to an eleventh embodiment of the present invention.

Figure 2:
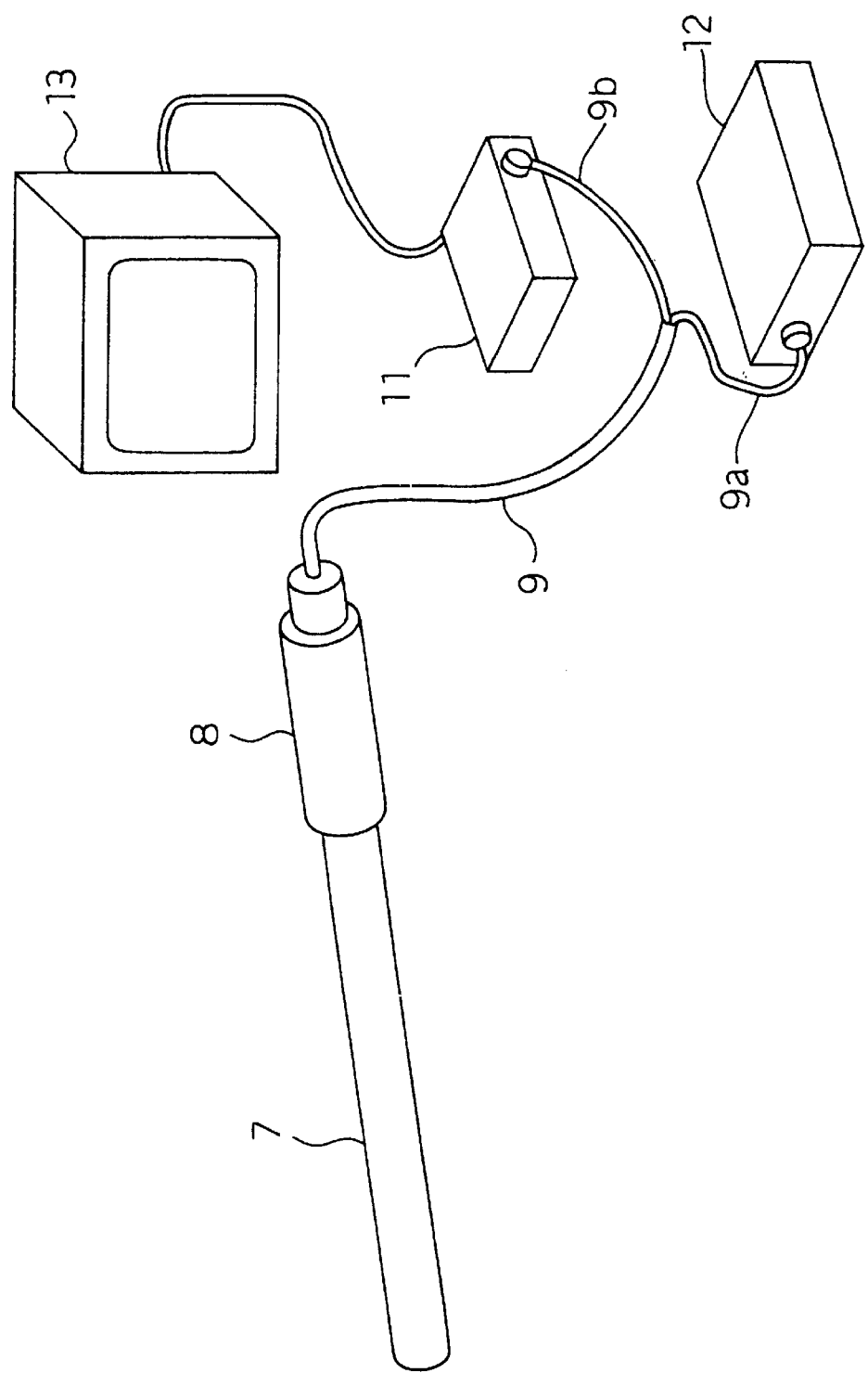
FIG. 2 is a general structural view of an endoscope system using the endoscope according to the first embodiment of the present invention.

1 light directing member
2 objective lens unit
2a objective lens
2b lens barrel (lens holder)
3 solid-state image sensing device
4 mounting member
5 circuit board
5a electrode portion
6 fixing member
7 insertion portion
8 connector
8a light directing connection portion
8b signal connection portion
9 connection cable
9a light guide cable
9b signal cable
10 sealing member
11 camera control unit
12 light source apparatus
13 monitor
14 image sensing unit
15 signal line
16 contact member
17 insulation member
17a, 17b through holes
18 positioning member
19 conduction means
20 relay optical system
21 adapter optical system
49, 54 V grooves
50 outer surface
51 front end surface
52 subject
53 tapered portion
55 reflecting member
56 conical portion
57 thin portion
61 light guide
61a light guide end surface
62 light diffusing device
63 image sensing optical system

BEST MODE FOR EXECUTING THE PRESENT INVENTION

Hereinafter, embodiments of the present invention will be described with reference to the drawings.

FIGS. 1 to 7 show a first embodiment of the present invention. FIG. 1 is a cross-sectional view showing the structure of an endoscope according to the first embodiment of the present invention. FIG. 1(A) is a cross-sectional view of an end of an insertion portion of the endoscope according to the first embodiment of the present invention. FIG. 1(B) is a cross-sectional view of a connector of the endoscope according to the first embodiment of the present invention.

In FIG. 1, reference numeral 1 represents an elongated light directing member which is a cylindrical member being hard enough to maintain its configuration, reference numeral 2 represents an objective lens unit, reference numeral 2a represents an objective lens, reference numeral 2b represents a lens barrel (lens holder) incorporating the objective lens 2a, reference numeral 3 represents a solid-state image sensing device, reference numeral 4 represents a mounting member incorporating the solid-state image sensing device 3, reference numeral 5 represents a circuit board electrically connected to the solid-state image sensing device 3, reference numeral 5a represents an electrode portion for electric connection formed at a rear end portion of the circuit board 5 (the power source and light source side will be referred to as a rear end and the insertion side, as a front end), reference numeral 6 represents a fixing member for fixing the circuit board 5 to the light directing member 1, reference numeral 7 represents an insertion portion, reference numeral 8 represents a connector connected to the insertion portion 7, reference numeral 8a represents a light directing connection portion, reference numeral 8b represents a signal connection portion, reference numeral 9 represents a connection cable, and reference numeral 10 represents a sealing member.

FIG. 2 is a general structural view of an endoscope system using the endoscope according to the first embodiment of the present invention. Reference numeral 9a represents a light guide cable. Reference numeral 9b represents a signal cable. Reference numeral 11 represents a camera control unit. Reference numeral 12 represents a light source apparatus. Reference numeral 13 represents a monitor.

Figure 3:
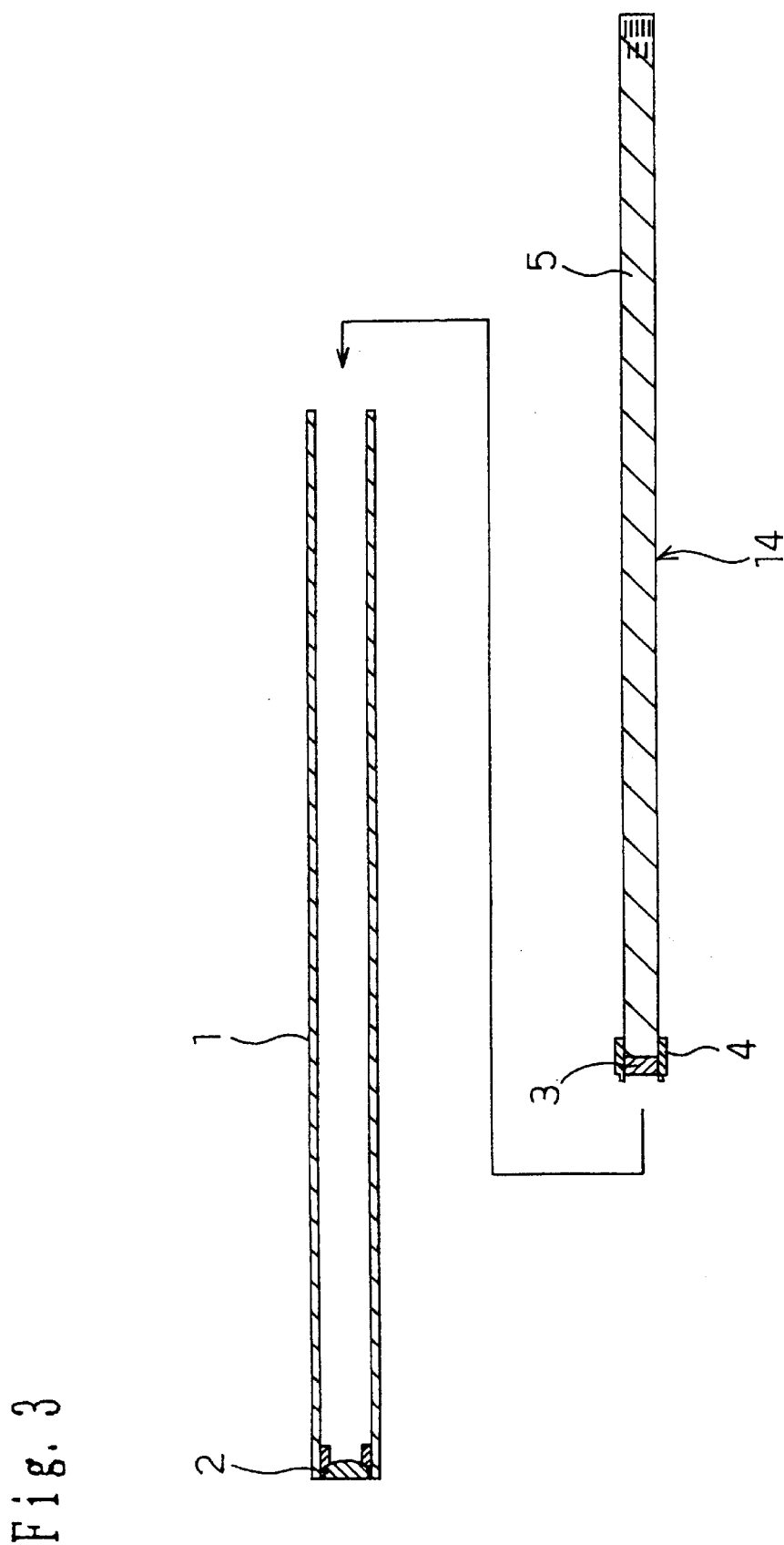
FIG. 3 is a cross-sectional view showing the structure of an image sensing unit of the endoscope according to the first embodiment of the present invention.

FIG. 3 is a cross-sectional view showing the structure of an image sensing unit of the endoscope according to the first embodiment of the present invention. Reference numeral 14 represents the image sensing unit comprising the solid-state image sensing device 3, the mounting member 4 and the circuit board 5.

The operation of the endoscope according to the first embodiment of the present invention and the endoscope system using the endoscope will hereinafter be described with reference to FIGS. 1 and 2.

The endoscope according to this embodiment is an electronic endoscope having the solid-state image sensing device 3 at the front end of the insertion portion 7. The illumination light is transmitted from the light source apparatus 11 through the light guide cable 9a, the light directing connection portion 8a and the light directing member 1 to illuminate the subject. The image of the illuminated subject is converted into an electric signal by the solid-state image sensing device 3 through the objective lens 2a. The electric signal converted by the solid-state image sensing device 3 passes through the circuit board 5 and is connected from the signal connection portion 8b to the camera control unit 10 by the signal cable 9b. After signal processing is performed, the subject image is displayed by the monitor 13.

Figure 4:
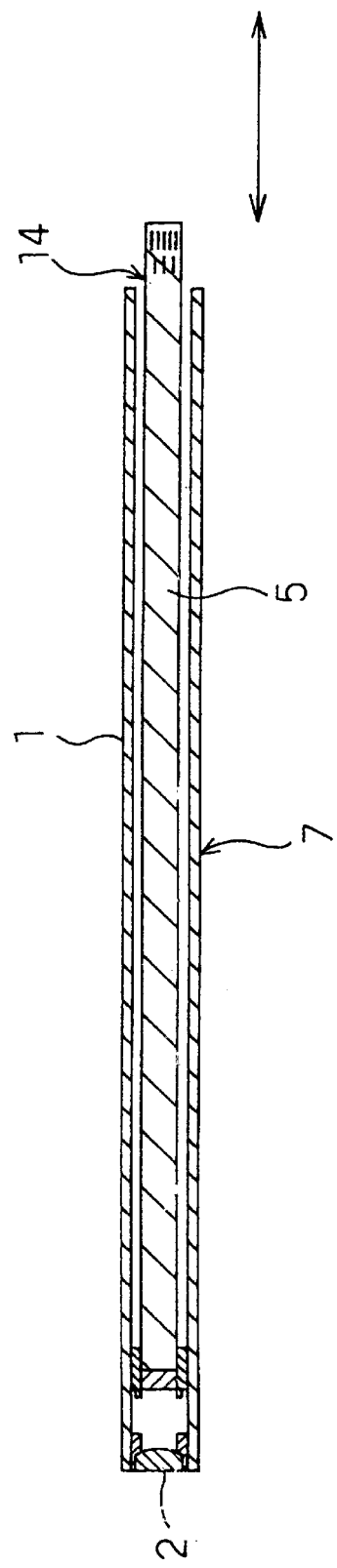
FIG. 4 is a cross-sectional view showing the structure of an insertion portion of the endoscope according to the first embodiment of the present invention.
Figure 5:
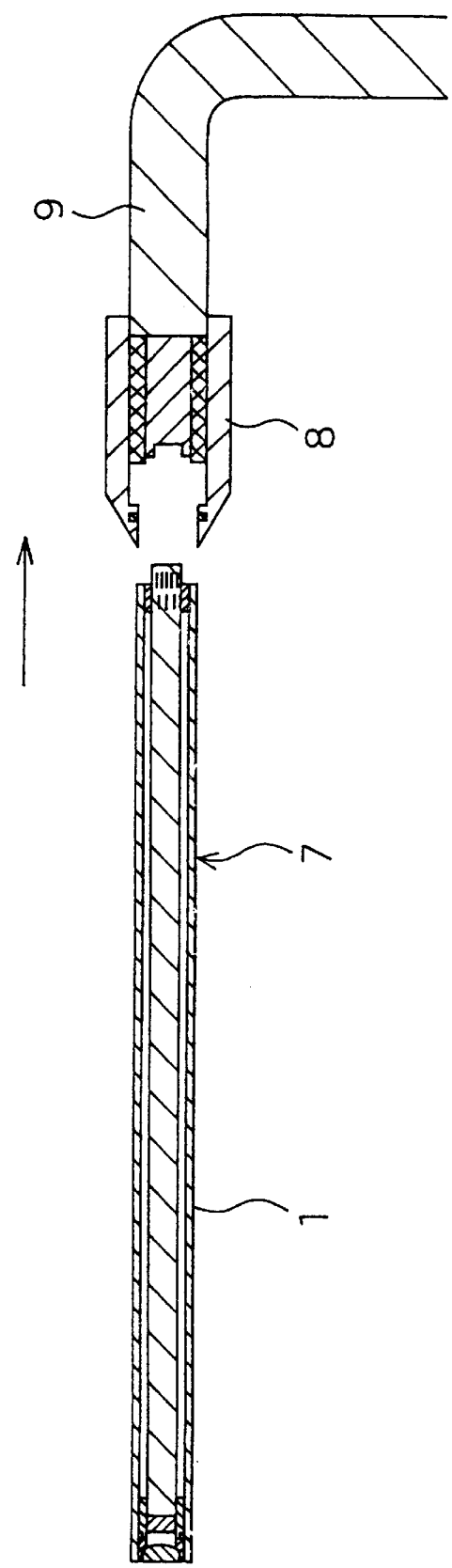
FIG. 5 is a cross-sectional view showing the structure (before connection) of the endoscope according to the first embodiment of the present invention.

Next, a detailed structure of the insertion portion of the endoscope according to this embodiment and a method of manufacturing the same will be described with reference to FIGS. 1 and 3 to 5. FIG. 4 is a cross-sectional view showing the structure of the insertion portion of the endoscope according to the first embodiment of the present invention. FIG. 5 is a cross-sectional view showing the structure (before) of the endoscope according to the first embodiment of the present invention.

The light directing member 1 may be made of a glass material; however, in view of the disposal after use, it is made of a combustible material, for example, a transparent resin such as acrylic. Moreover, the light directing member 1 may be oval in cross section under special conditions such as a smaller diameter; however, a cylindrical pipe being simple in configuration is desirable because it is inexpensive and the structure is simplified.

As shown in FIG. 3, the objective lens unit 2 comprises the objective lens 2a and the lens barrel (lens holder) 2b and is hermetically joined to the front end portion of the light directing member 1 in advance. Thereafter, as shown in FIG. 4, the image sensing unit 14 comprising the solid-state image sensing device 3, the mounting member 4 and the circuit board 5 is inserted and aligned with the objective lens unit 2 by use of the rear end side of the circuit board 5. When the alignment is completed, the image sensing unit 14 is fixed by means such as screws provided on the lens barrel 2b and the mounting member 4. Then, the circuit board 5 is fixed to the light directing member 1 by use of the fixing member 6.

The insertion portion 7 may be assembled through the following steps: After the objective lens unit 2 and the image sensing unit 14 are aligned and fixed to each other, they are inserted into the light directing member 1. Then, the objective lens unit 2 and the light directing member 1 are joined at the front end side and the circuit board 5 is fixed to the light directing member 1 by use of the fixing member 6 at the rear end side of the insertion portion 7.

The method of connecting the objective lens unit 2 and the light directing member 1 and the method of joining the fixing member 6 and the light directing member 1 include a joining method not using adhesive such as ultrasonic welding. The light directing member 1, which also transmits the light for irradiation, may be bonded by use of a photo-setting adhesive such as a UV adhesive. When a photo-setting adhesive is used, an advantage is obtained that the parts such as the objective lens unit 2 and the fixing member 6 can be assembled while being accurately positioned because it is possible to harden the adhesive for bonding and fixing after the parts are inserted into the light directing member 1.

Thus, the insertion portion 7 can be comparatively easily assembled because it has a very simple structure and configuration broadly divided into two or three units, for example, the light directing member 1, the objective lens unit 2 and the image sensing unit 14 comprising the solid-state image sensing device 3 and the circuit board 5, etc.

The assembled insertion portion 7 is used being connected through the connector 8 to the connection cable 9 comprising the light guide cable 9a and the signal cable 9b as shown in FIG. 5. The connector 8 has the sealing member 10 such as an O ring and by being connected to the connector 8, the insertion portion 7 becomes hermetic so that the inside thereof is not contaminated. In stably fixing the rear end side of the insertion portion 7 to the circuit board 5 by use of the fixing member 6, if the insertion portion 7 is made hermetic by use of an epoxy adhesive, etc., the insertion portion 7 is double-sealed in combination with the sealing by the sealing member 10 of the connector 8, so that the possibility will further decrease that the inside of the insertion portion 7 is contaminated with the patient's blood, etc.

The connector 8 comprises the light directing connection portion 8a and the signal connection portion 8b. The light directing connection portion 8a to be connected to the light directing member 1 and the signal connection portion 8b to be connected to the electrode portion 5a of the circuit board 5 have configurations and sizes in accordance with those of the light directing member 1 and the electrode portion 5a, respectively. By forming the light directing connection portion 8a so as to have an annular shape in which the signal connection portion 8b is provided, the illumination light is efficiently transmitted and the connector 8 can be formed to have a simple structure being excellent in operability.

Next, a concrete structure of the signal connection portion 8b will be described with reference to FIG. 6. FIG. 6(B) is a cross-sectional view showing the structure of the signal connection portion of the endoscope according to the first embodiment of the present invention. Reference numeral 15 represents signal lines constituting the signal cable 9a. Reference numeral 16 represents a V-shaped cross section contact member elastically deformed so as to come into contact with the electrode portion 5a of the circuit board for conduction. Reference numeral 17 represents an insulation member for connecting and fixing the contact member 16. Reference numerals 17a and 17b represent through holes provided in the insulation member 17. Reference numeral 18 represents a positioning member for positioning the electrode portion 5a and the contact member 16 so that the contact therebetween is ensured. Reference numeral 19 represents connection wiring formed on the insulation member 17. FIG. 6(A) is plane views of components of FIG. 6(B).

In FIG. 6, the signal connection portion 8b is structured so that the contact member 16 is in contact with the electrode portion 5a of the circuit board 5 so as to be electrically connected to the signal lines constituting the signal cable 9a. The contact member 16 has pressing mechanism means which is elastically deformed so as to be pressingly in contact with the electrode portion 5a for electrical conduction. A plurality of contact members 6 are arranged in correspondence with the arrangement of the electrode portions 5a.

The signal lines 15 and the contact members 16 are electrically connected and fixed to the through holes 17a provided in the insulation member 17 and to the through holes 17b provided in the insulation member 17 in correspondence with the positions of the electrode portions 5a, respectively, by a method such as soldering. In inserting the insertion portion 7 into the connector 8, positioning is performed by the positioning member 18 so that the electrode portions 5a are surely in contact with the contact members 16. The connector 8 is provided with a lock mechanism (not shown) in order that the insertion portion 7 and the connector 8 are surely fixed so as not to be disconnected when the endoscope is used.

There is a case where the number of electrodes of the electrode portions 5a increases as the diameter of the insertion portion 7 of the endoscope decreases and a plurality of electrode portions 5a are arranged in a plurality of rows in the direction of insertion. Even in such a case, by providing the above-described structure, the signal connection portion 8b can be structured so as to be thin and easy to insert. Since it is unnecessary to provide a separate connector on the side of the insertion portion 7 like in the prior art, the structure of the insertion portion 7 is simplified and the price is reduced.

Further, by providing the contact member 16 with the pressing mechanism means, excellent electric connection is obtained even if the number of electrodes of the electrode portions 5a is great and the electrical connection with the circuit board 5 is obtained with a single motion. While the contact member 16 does not necessarily have the pressing mechanism means, the structure having the pressing mechanism means like the one described in this embodiment is more effective because excellent electrical connection is obtained and the insertion is easy.

As the conduction means 19 for electrically connecting the signal lines 15 and the contact members 16, for example, a pattern wiring formed on the insulation member 17 is used. That is, the conduction means 19 is formed on the insulation member 17 by use of a pattern wiring which connects the through holes 17a for connecting and fixing the signal lines 15 and the through holes 17b for connecting and fixing the contact members 16 corresponding to the signal lines 15.

By applying the pattern wiring used for the circuit mounting and the semiconductor mounting to the conduction means 19, the signal connection 8b can be manufactured in accordance with the arrangement pattern of the electrode portions 5a even if the arrangement pattern is fined and complicated. This is also a feature of this embodiment.

When the electrode portions 5a are comparatively large, the signal connection portion 8b may be structured as shown in FIG. 7. FIG. 7(B) is a cross-sectional view showing the structure of another signal connection portion of the endoscope according to the first embodiment of the present invention. FIG. 7(A) is plane views of components of FIG. 7(B)

Specifically, the electrode portions 5a are arranged in the front and rear rows in a staggered configuration. That is, the electrode portions 5a are staggered so as not to be situated on a straight line (X) which is in the direction of insertion. The contact members 16 and the signal lines 15 are electrically connected and fixed in the through holes 17a by a method such as soldering. The contact member 16 extends from the through hole 17a serving as connection and fixing means to the vicinity of the electrode portion 5a and is bent downward at a desired angle through the other through hole 17b so as to have a spring property, thereby also realizing a pressing mechanism.

This structure is suitable for mass production because the contact member 16 can be manufactured from a strip-form metal thin plate by bending and it is unnecessary to provide a separate conduction means like in the embodiment of FIG. 6 since a part of the contact member 16 is also used as the conduction means 19.

In summary, this embodiment is largely different from the prior art in that the hollow cross section, i.e. cylindrical light directing member 1 being hard enough to maintain its configuration is used as the exterior structure of the insertion portion 7 and is also used as the light guide which has conventionally been provided inside the insertion portion 7, and that the circuit board 5 extending from the solid-state image sensing device 3 to the rear end portion of the light directing member 1 is used and the electrode portions for disconnectable electrical connection with the signal cables are formed at the rear end portion of the circuit board 5. The workings and effects thereof will be described hereinafter.

Typical structure of the hard endoscope used for surgery is such that an objective lens, a structure incorporating image transmission lens units comprising a plurality of rod lenses and a light guide comprising a multiplicity of optical fibers are mounted in a metal exterior structure. With this structure, the endoscope is optically and structurally very complicated, the manufacture is very intricate and the number of parts is great, so that it cannot be helped that the endoscope is expensive.

In the case of the electronic endoscope in which a CCD is disposed at the front end, the endoscope is optically simplified because the image transmission lens units are unnecessary; however, since wiring and connectors for connecting signals are necessary, it cannot be helped that the endoscope is structurally complicated. Further, a disposable endoscope has been proposed in which the metal exterior structure is replaced with an insertion portion configuration into which the illumination optical system and the image sensing optical system are integrated by use of resin. However, in any case, the price reduction is limited because the endoscope is structurally complicated.

On the contrary, in the endoscope of this embodiment, since the hollow cross section light directing member 1 is used as the exterior structure of the insertion portion 7 and is also used as the light guide which has conventionally been provided inside the insertion portion 7, the light guide which has conventionally been used as a separate member is unnecessary.

Since a cylindrical pipe being simple in configuration is used as the light directing member 1 as it is and the electrode portions 5a for disconnectable electrical connection with the signal cables are formed at the rear end portion of the circuit board 5 electrically connected to the solid-state image sensing device 3, signal connection and light direction connection can be simultaneously made at the rear end portion of the insertion portion 7, so that the connector 8 serving as the connection portion can be simplified in structure.

Consequently, the insertion portion of the endoscope is easy to assemble and the price is reduced and with respect to the connection with the connection cable, signal connection and light direction connection can be made with a single motion and the configuration of the operation portion can be simplified, so that the operability during use improves. When the light directing member 1 is made of a combustible material such as a resin-made pipe, it is suitable for a disposable endoscope because it can be disposed of by incineration.

While it is also a feature of the present invention that the circuit board 5 electrically connected to the solid-state image sensing device 3 is formed to extend from the solid-state image sensing device 3 to the rear end portion of the light directing member 1, the present invention is further advantageous over the prior art where a multiplicity of optical fibers not using a resin-made pipe like the light directing member 1 is used as the light guide and incorporated in a metal exterior member, in that incorporation of the image sensing unit 13 is easy and that the connection with the signal connection portion 8b is easy.

According to the degree of the hermeticity of the insertion portion 7, the present invention is applicable to the conventional endoscopes of a type (reuse type) which is impervious to repetitive disinfection and of a type which is impervious to several times of disinfection.

While a case where the light directing member 1 is used as the exterior structure of the insertion portion 7 has been described in this embodiment, similar effects are obtained by an arrangement in which after parts such as the objective lens unit 2 and the solid-state image sensing device 3 are incorporated in the light directing member 1, a sheath is applied over the light directing member 1.

Next, a second embodiment of the present invention will be described with reference to the drawings.

FIG. 8(A) is a cross-sectional view showing the structure of an endoscope according to the second embodiment of the present invention. FIG. 8(B) is a cross-sectional view showing a connector 8. In FIG. 8, reference numeral 20 represents a relay optical system for transmitting a subject image, and reference numeral 21 represents an adapter optical system for imaging the subject image transmitted from the relay optical system 20 onto the solid-state image sensing device 3.

The insertion portion 7 of the endoscope of this embodiment is an optical inspection tube comprising the light directing member 1, the objective lens unit 2, the relay optical system 20 and the adapter optical system 21. Unlike in the first embodiment, the solid-state image sensing device 3 is provided not at the front end of the insertion portion 7 but on the side of the connector 8.

It is desired that not only the light directing member 1 but also the objective lens unit 2, the relay optical system 20 and the adapter optical system 21 be made of a combustible resin material such as acrylic.

The operation of the endoscope using the insertion portion structured as described above will hereinafter be described with reference to FIG. 8.

The subject image captured through the objective lens unit 2 is transmitted by the relay optical system 20 and imaged by the adapter optical system 21 onto the solid-state image sensing device 3 provided inside the connector 8. The principle from the succeeding signal transmission to the display on the monitor is the same as that of the first embodiment. The arrangement and the principle for transmitting the illumination light are also the same as those of the first embodiment.

With respect to the method of manufacturing the insertion portion 7, the light directing member 1 which also transmits the light for irradiation can be bonded by use of a photosetting adhesive such as a UV adhesive like in the first embodiment. Particularly, for the bonding of the relay optical system 20, a method such as ultrasonic welding is difficult to use because the relay optical system 20 comprising a multiplicity of lenses requires accurate positioning and is necessarily disposed at a central portion of the insertion portion 7. Therefore, the manufacturing method using the photo-setting adhesive is more effective.

This embodiment is largely different from the conventional embodiments and the first embodiment in that the insertion portion 7 is wholly made of a resin material such as acrylic and can be disposed of by incineration. This embodiment is more suitable for use as a disposable endoscope in that medical waste can be reduced.

Moreover, like in the first embodiment, similar effects are obtained by the arrangement in which after parts such as the objective lens unit 2 and the relay optical system 20 are incorporated in the light directing member 1, a sheath is applied over the light directing member 1.

Figure 9:
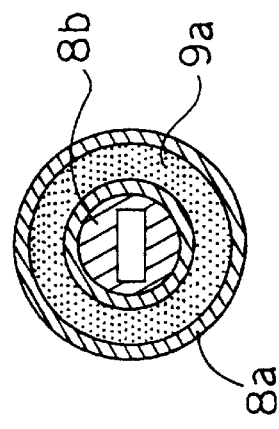
FIG. 9 is a cross-sectional view showing a connector-centered structure of an endoscope according to a third embodiment of the present invention.
Figure 9:
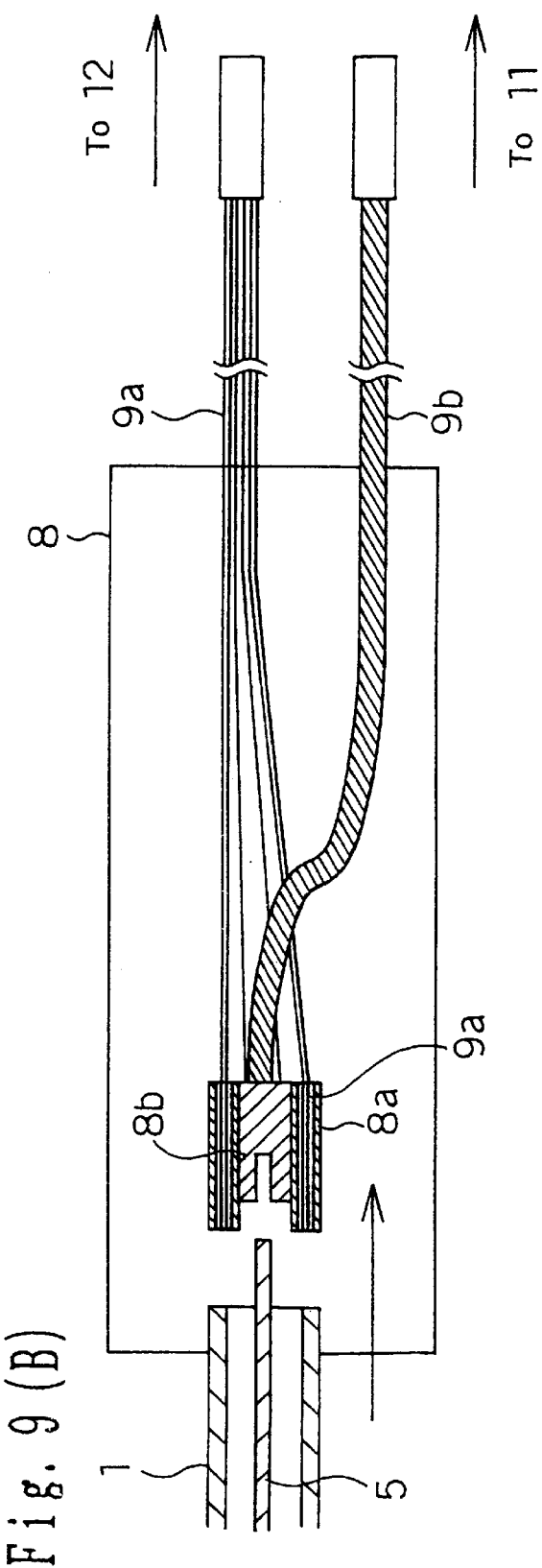

FIG. 9(B) is a cross-sectional view mainly showing the connector 8 in a third embodiment of the present invention. In the third embodiment, while the signal connection portion 8b is similar to that of the above-described first embodiment of FIG. 6, the structure of the light directing connection portion 8a is different. That is, the size and configuration of the light exit end of the light directing connection portion 8a is the same as the size and configuration of the light incident end of the light directing member 1. With this structure, the light incident on a light directing cable 9a is transmitted to the light directing member 1 with minimum loss. In the third embodiment, the signal connection portion 8b is also inside the light directing connection portion 8a.

FIG. 9(A) is a cross-sectional view of the light directing connection portion 8a and the signal connection portion 8b.

FIG. 10(B) is a cross-sectional view mainly showing the connector 8 in a fourth embodiment of the present invention. In the fourth embodiment, while the signal connection portion 8b is similar to that of the above-described first embodiment of FIG. 6, the structure of the light directing connection portion 8a is different. That is, the light directing connection portion 8a comprises three members 8a1, 8a2 and 8a3. The size and configuration of a light incident end 8a2' in the member 8a2 situated on the light incident side are the same as the size and configuration of a light exit end 9a1 of the light directing cable 9a. The size and configuration of the light exit end in the member 8a1 situated on the light exit side are the same as the size and configuration of the light incident end of the light directing member 1. The two members 8a1 and 8a2 connect light incident end and light exit end and are connected by the optical fiber 8a3. A cylinder 91 is fixed to the light exit end 9a1 of the light directing cable 9a and a cylinder 81 is fixed to the light incident end 8a2' of the light directing connection portion 8a. The cylinder 81 is detachably inserted in the cylinder 91. With this structure, the connector 8 is connectable to and disconnectable from the light directing cable 9a.

As a result, according to the fourth embodiment, the general versatility of the present invention using other manufacturer's cable as the light directing cable and using other manufacturer's light source is improved.

FIG. 10(A) is a cross-sectional view of the light directing connection portion 8a and the signal connection portion 8b.

Figure 11:
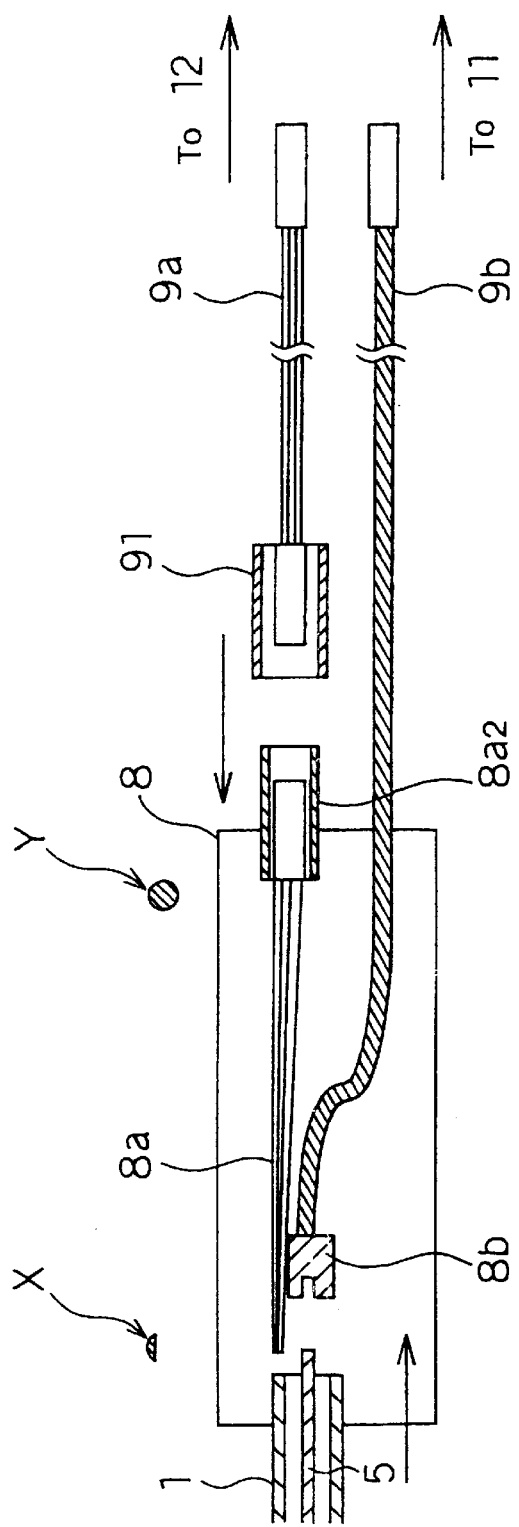
FIG. 11 is a cross-sectional view showing a connector-centered structure of an endoscope according to a fifth embodiment of the present invention.

FIG. 11 is a cross-sectional view mainly showing the connector 8 in a fifth embodiment of the present invention.

This embodiment is substantially similar to the fourth embodiment but is different therefrom in that the light directing member 1 side member 8a1 of the light directing connection portion 8a does not exist and instead, the thickness of the light directing member 1 side (light exit end side) end of the light directing connection portion Ba is the same as the cylindrical thickness of the light directing member 1. The arrow X in FIG. 11 shows the thickness and configuration. The cross section of the member 8a2 side is shown by the arrow Y for reference.

Figure 12:
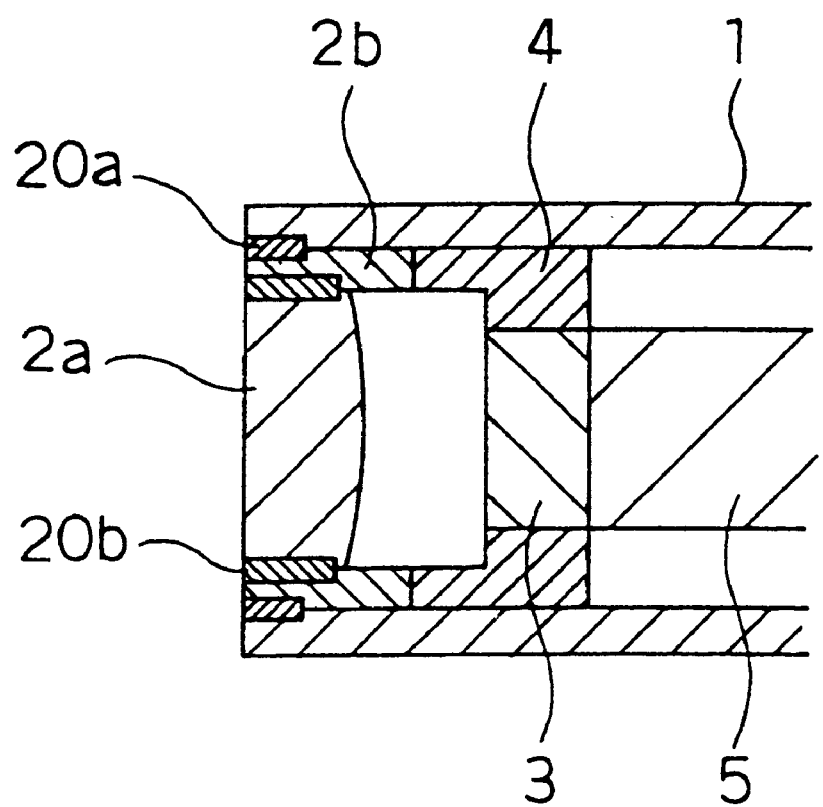
FIG. 12 is a cross-sectional view showing a connector-centered structure of an endoscope according to a sixth embodiment of the present invention.

FIG. 12 is a cross-sectional view mainly showing the front end of the insertion portion 7 in a sixth embodiment of the present invention.

In the sixth embodiment, the lens barrel (lens holder) 2b is inserted in the front end of the light directing member 1 and the lens 2a is inserted in the lens barrel 2b. In the rear of the lens barrel 2b, the mounting member 4 is continuously inserted.

A hermetic structure 20a is provided between the light directing member 1 and the lens barrel 2b, and a hermetic structure 20b is provided between the lens barrel 2b and the lens 2a. These hermetic structures surely prevent blood and body fluid from entering the insertion portion 7 and prevent pollution of the CCD 3.

While the insertion portion 7 may be made hermetic by a given method, for example, ultrasonic welding can be used.

When the members between which the hermetic structure is provided are made of the same material, the hermetic sealing is easier. In the conventional endoscope, since the lens barrel is made of a metal and the exterior member is made of glass, it is difficult to provide a hermetic structure there between.

Figure 13:
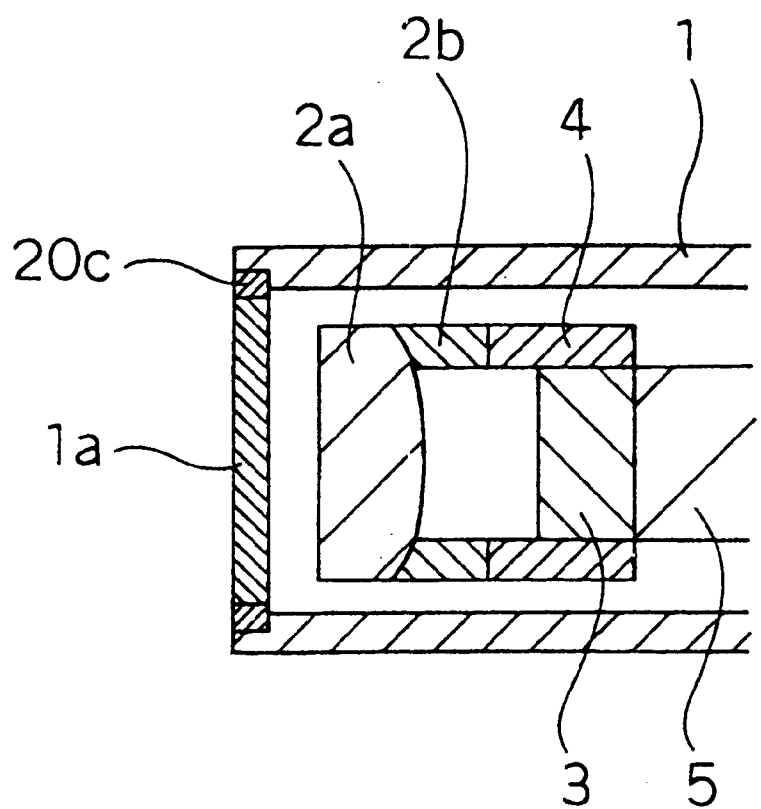
FIG. 13 is a cross-sectional view showing a connector-centered structure of an endoscope according to a seventh embodiment of the present invention.

FIG. 13 is a cross-sectional view mainly showing the front end of the insertion portion 7 in a seventh embodiment of the present invention.

The seventh embodiment is different from the above-described sixth embodiment in that the lens 2a and the lens barrel 2b are not hermetic with respect to the light directing member 1 and instead, an optical window 1a is attached to the front end of the light directing member 1 and a hermetic structure 20c is provided between the optical window 1a and the light directing member 1. The details of the structure are the same as those of the sixth embodiment.

Figure 14:
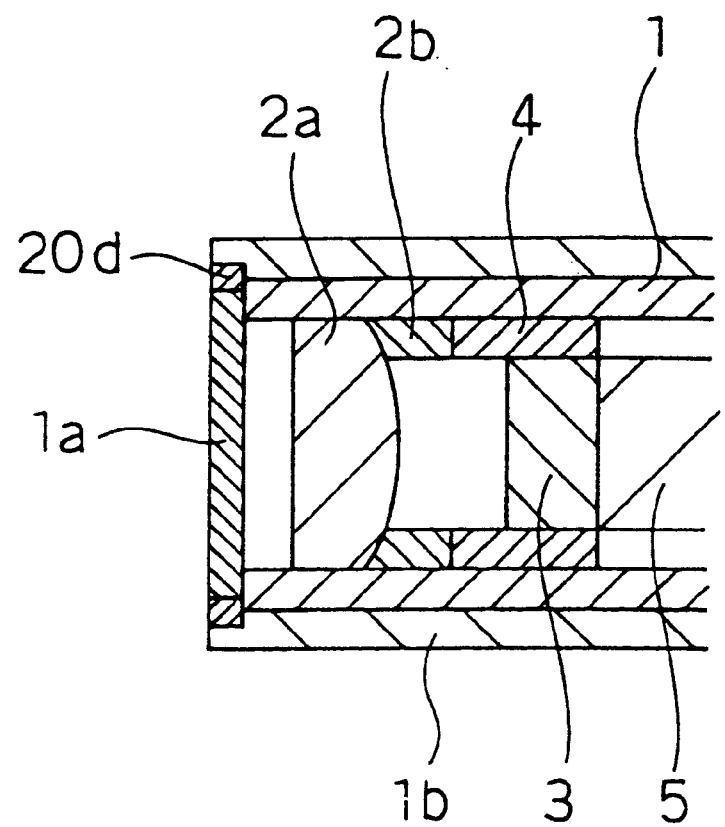
FIG. 14 is a cross-sectional view showing a connector-centered structure of the endoscope of the present invention.
Figure 15A:
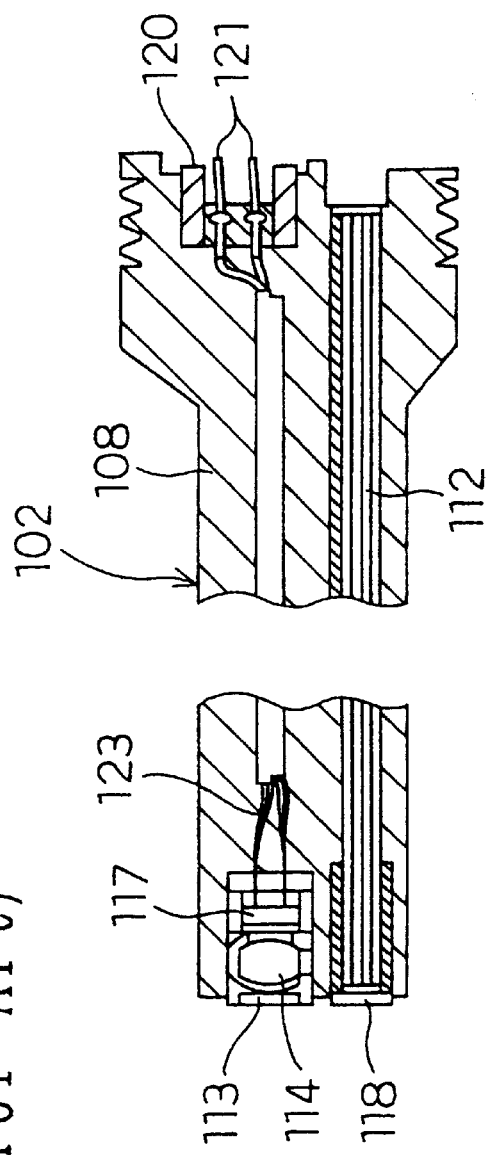
FIG. 15 is a cross-sectional view and a general structural view of a conventional endoscope suitable for use as a disposable endoscope.
Figure 15B:
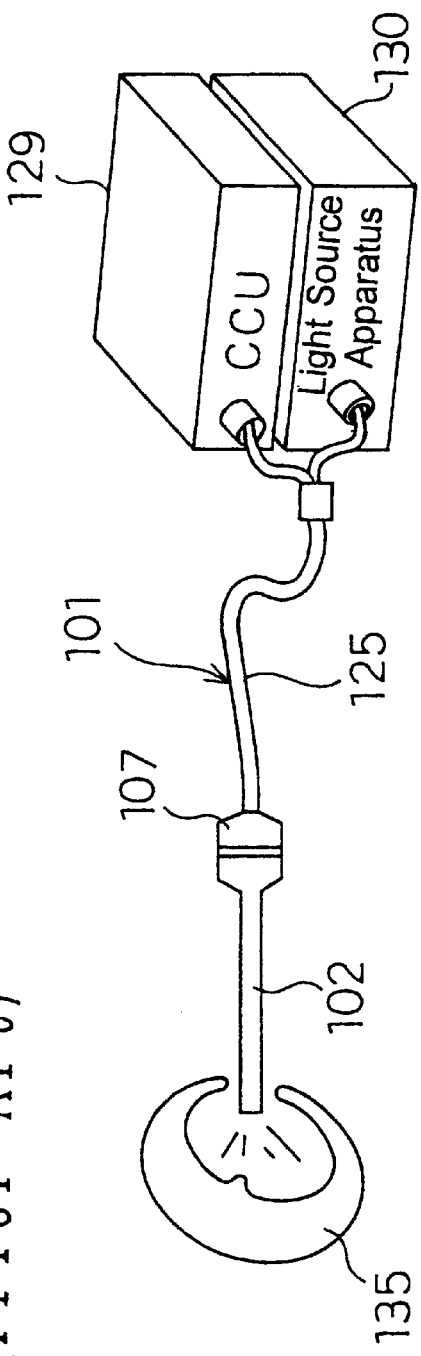
Figures 16A, 16B, 16C:
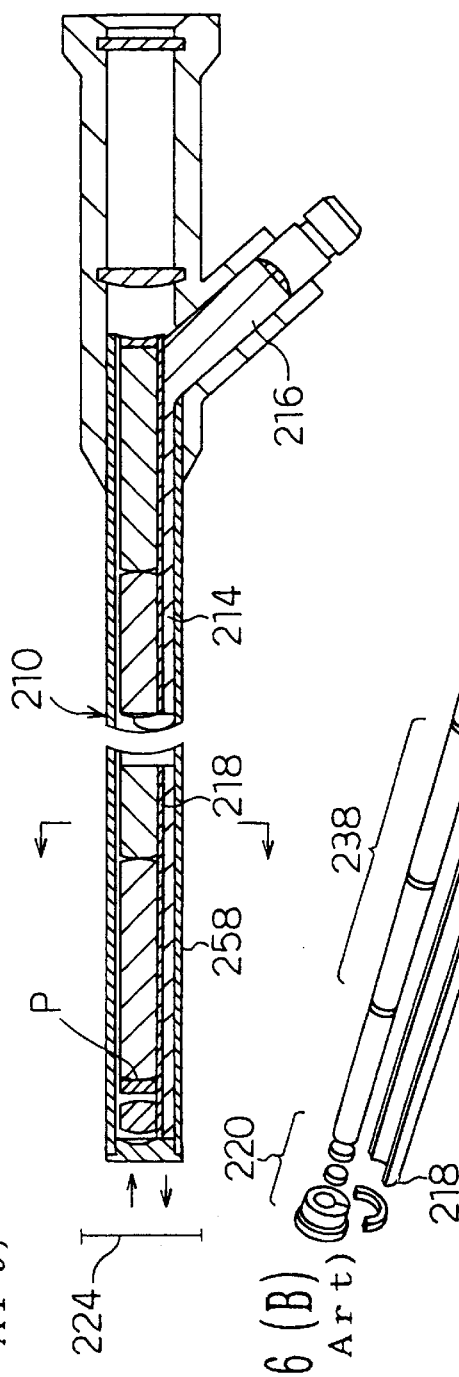
FIG. 16 is a side cross-sectional view, an exploded perspective view and a partial enlarged cross-sectional view of a conventional endoscope suitable for use as a disposable endoscope.

FIG. 14 shows an example in which an exterior member 1b is attached outside the light directing member 1 and a hermetic structure 20d is provided between the exterior member 1b and the optical window 1a.

As described above, according to the endoscope and the method of manufacturing the same of the above-described first to seventh embodiments:

(1) The light guide member which has conventionally been used as a separate member is unnecessary. Moreover, the insertion portion, which is very simple in structure and configuration, is comparatively easy to assemble and is reduced in price.

(2) When signal connection and light direction connection can be simultaneously made at the rear end portion of the insertion portion, the connector serving as the connection portion can be simplified in structure. Moreover, even when the number of electrodes of the electrode portions increases and a plurality of electrodes are arranged in a plurality of rows, the signal connection portion can be structured so as to be thin and easy to insert. Consequently, the insertion portion of the endoscope is easy to assemble and reduced in price, and with respect to the connection with the connection cable, signal connection and light direction connection are made with a single motion and the configuration of the operation portion can be simplified, so that the operability during use improves.

(3) When the insertion portion is wholly or mostly made of a combustible material, the endoscope is suitable for a use such that the insertion portion is disposed of by incineration.

Moreover, since whether the endoscope is new or used is apparent at a glance of the condition of the terminal member, these embodiments are suitable for use as an endoscope to be thrown away after one use.

(4) Since the light directing member also transmits the irradiation light comprising ultraviolet rays, when a photo-setting adhesive is used, the parts such as the objective lens unit and the fixing member can be assembled while being accurately positioned by hardening the adhesive for bonding and fixing after the parts are inserted into the light directing member.

Since an easy-to-manufacture and inexpensive endoscope of a type being thrown away after one use or a type being thrown away after a limited number of uses and a method of manufacturing the same are provided by the above-mentioned workings, the industrial value of the present invention is great.

Next, an eighth embodiment of the endoscope of the present invention will be described with reference to the drawings.

Figure 17B:
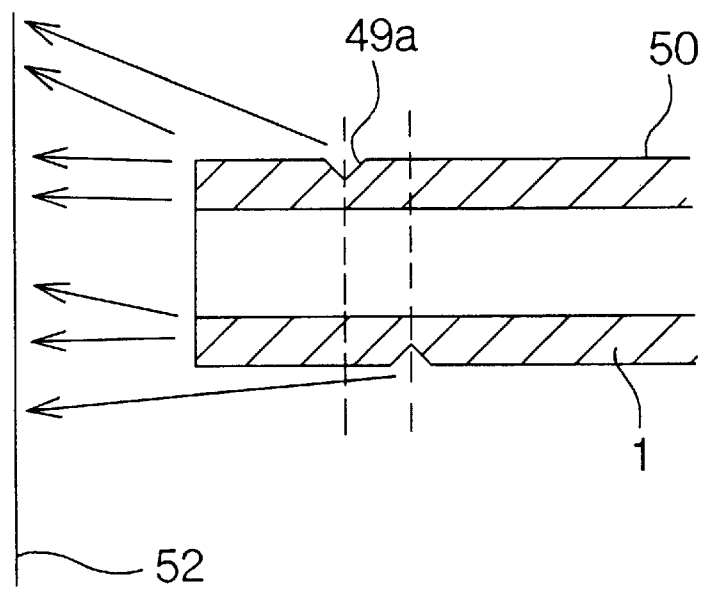
FIG. 17b is an enlarged cross-sectional view of a front end portion of a light directing member of an endoscope according to an eighth embodiment of the present invention showing a spiral grove.
Figure 21:
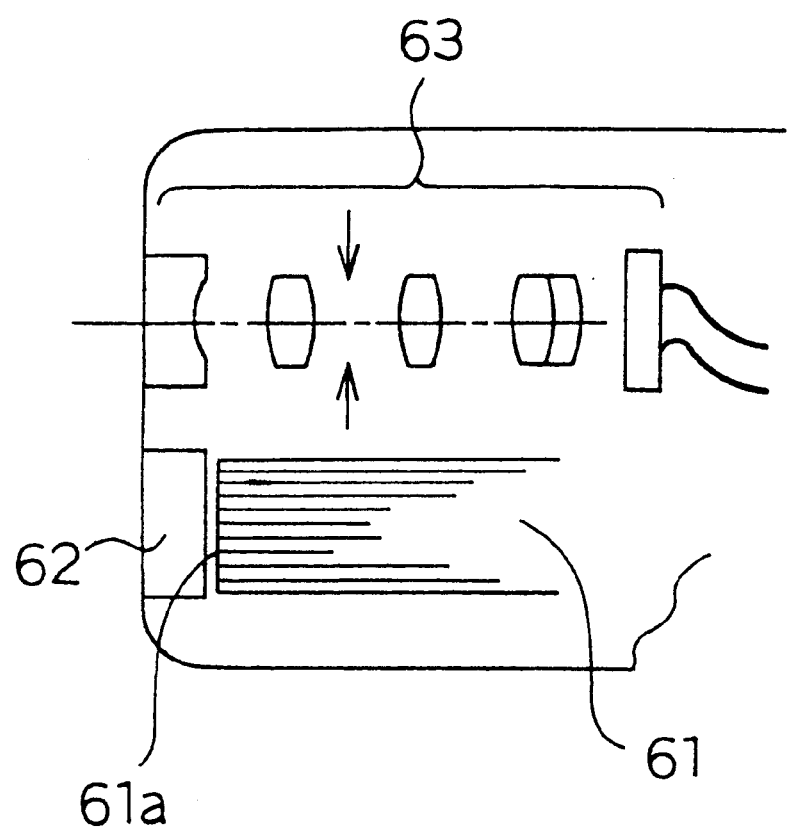
FIG. 21 is a structural view of an end portion of an example of a conventional endoscope.

FIG. 17a is a view showing the eighth embodiment and shows an enlarged cross-sectional view of the front end portion of the light directing member 1. A V groove 49 as an example of a light dispersing portion is concentrically formed on an outer surface 50.

For most of the illumination light having reached the V groove 49 and the illumination light reflected at the V groove 49, the total reflection condition of light is broken as a result of a change of the angle of incidence on the surface of the light directing member 1, so that light is released from the light directing member 1 to illuminate a subject 52 (light shown by the dotted lines).

The illumination light which is not released from the light directing member 1 by the V groove 49 but is directed through the light directing member 1 reaches a front end surface 51 while being repetitively total-reflected again. The light having reached the front end surface 51 is released from the front end surface 51 and mainly illuminates an area inside the area illuminated by the light released from the V groove 49 (light shown by the solid lines).

The image of the illuminated subject 52 passes through the objective lens 2a and is converted into an electric signal by the solid-state image sensing device 3. Various signal processings are performed on the electric signal and the subject image is displayed on the monitor.

According to the endoscope of this embodiment, since both the illumination light from the outer surface of the light directing member 1 and the illumination light from the front end surface of the light directing member 1 can be used by using the hollow and elongated light directing member 1, an extremely wide area can be excellently illuminated.

Moreover, since the distribution of the illumination can be easily optimized by changing the configuration or the position of the outer surface 50, the illumination can be easily uniformized.

Further, since it is unnecessary to use the complicated and expensive light diffusing device like in the prior art and the light dispersing effect is added only by integrally processing the light directing portion, the structure is simplified and the cost is reduced.

The groove of the light dispersing portion is not necessarily the V groove but may be a U groove. Moreover, it is not necessarily concentrically formed but may be spirally formed as shown by groove 49a in FIG. 17b. The light dispersion portion is not necessarily provided on the outer surface of the light directing member but may be provided on the inner surface of the light directing member. Moreover, light may be dispersed by forming minute projections and depressions of approximately several tens of nanometers to several hundreds of micrometers on the outer surface, on the inner surface or on the front end surface of the light directing member 1.

That is, the light dispersing member may have any configuration that can disperse outward the illumination light directed through the light directing member 1 by breaking the total reflection condition of the illumination light.

FIG. 18 is an enlarged cross-sectional view of a front end portion of a light directing member of an endoscope according to a ninth embodiment of the present invention. The outside diameter of the front end portion of the light directing member 1 gradually decreases toward the front end surface 51 to form a tapered portion 53.

The illumination light directed while being total-reflected through the light directing member 1 has its total reflection condition broken by the tapered portion 53 and is released outside from the light directing member 1. Part of the illumination light is not released at the tapered portion 53 but is directed through the light directing member 1 to reach the front end surface 51. This light is released from the front end surface 51 to illuminate the subject 52.

Thus, by forming the front end portion of the light directing member 1 so as to be tapered, the illumination light can be easily dispersed at the outer surface of the light directing member 1.

Since the tapered outer surface like that of this embodiment is a plane surface, it is very easy to disinfect compared with the surface having a complicated configuration or projections and depressions. Moreover, since it is tapered, it is easily inserted into the patient's body through a tracker at the time of surgery.

While the case of a linearly tapered front end portion has been described, the present invention is not limited thereto; the front end portion may be curvedly tapered or may have a configuration which is a combination of linear and curved tapers.

FIG. 19(A) is an enlarged cross-sectional view of a front end portion of a light directing member of an endoscope according to a tenth embodiment of the present invention. A V groove 54 is concentrically formed on the front end surface 51. FIG. 19(B) shows the V groove 54 viewed from the direction of the axis of the light directing member 1.

When the illumination light directed while being total-reflected through the light directing member 1 reaches the front end surface 51, a refraction effect comparable to that of a concave lens is generated by the V groove 54 formed on the front end surface 51, so that the light released from the front end surface 51 illuminates a wider area.

In the conventional arrangement using the silica optical fiber bundle, in order to realize such wide area illumination, it is necessary to provide a separate optical device or to precisely process the end surface of the optical fiber bundle. This greatly increases the cost.

According to this embodiment, since the V groove 54 can be integrally formed with the light directing member 1 by processing the light directing member made of a resin such as acrylic, it is unnecessary to provide a dedicated optical device.

The groove is not necessarily V-shaped. Moreover, it is not necessarily concentrically formed but may be spirally formed. The number of grooves is not necessarily one but a plurality of grooves may be formed.

FIG. 20(A) is a cross-sectional view of the light directing member 1 of an endoscope according to an eleventh embodiment of the present invention. FIG. 20(B) is an enlarged cross-sectional view of a front end portion thereof. On the outer surface 50, a conical portion 56 and a thin portion 57 formed by decreasing the wall thickness of the light directing member 1 are integrally formed with the light directing portion 1. On the inner surface of the light directing member 1, a reflecting member 55 is provided.

The illumination light directed while being total-reflected through the light directing member 1 has its total reflection condition broken by the conical portion 56 and is released outward from the light directing member 1 (dotted lines) and part of the illumination light is released inward from the light directing member 1 (solid lines).

The illumination light released inward advances toward the lens barrel 2a for holding the objective lens 2 and the mounting member 4 of the solid-state image sensing device 3 provided in the light directing member 1 (see FIG. 1).

The reflecting member 55 reflects the illumination light released toward the lens barrel 2b and the mounting member 4 at a high reflectance toward the subject 52. For this reason, the illumination light directed through the light directing member 1 can be sufficiently effectively used.

While the case of a conical light dispersing portion has been described in this embodiment, the arrangement may be used in which the light dispersing portion is provided on the outer surface or the inner surface of the light directing member 1 like in the above-described embodiments.

It is preferable that the reflecting member be made of a material having a high reflectance, for example, an aluminum film. This is because the aluminum film is very inexpensive and a high reflectance is easily obtained.

The inward release of the illumination light is not only caused by the outer surface configuration shown in this embodiment but also caused in almost all the cases where the total reflection condition is broken. Therefore, the present invention is effective not only for this embodiment but for all that have the light dispersing portion like the above-described embodiments.

Next, a twelfth embodiment of the present invention will be described. In this embodiment, the lens barrel 2b for holding the objective lens 2a and the mounting member 4 for holding the solid-state image sensing device 3 are provided inside the light directing member 1, and a high reflectance material such as aluminum is used as the material of the lens barrel 2b or the mounting portion 4, or the surface coating material of the members.

Since it is unnecessary to provide a separate high-reflectance member like in the eleventh embodiment because of this feature, the insertion of the high-reflectance member is unnecessary, so that the mounting process can be simplified.

Moreover, it is very preferable to form minute projections and depressions of approximately several tens of nanometers to several hundreds of micrometers on the surface of the lens barrel 2b or the mounting member 4 by knurling or sand-blasting.

That is, since the light released inward from the light directing member 1 is reflected being uniformized by the minute projections and depressions, more excellent illumination is realized.

By the formation of the minute projections and depressions, the strength of bonding between these members and the light directing member 1 is improved, for example, when they are bonded by use of a UV resin.

According to this embodiment, illumination is uniformized without the provision of the minute projections and depressions on the outer surface of the light directing member 1. Since the surface of the light directing member 1 can be formed smooth for this reason, the surface of the light directing member is highly resistant to contamination.

Although not shown, the lens barrel 2b or the mounting member 4, and the light directing member 1 may be fixed by threading the outer surface of the lens barrel 2b or the mounting member 4 made of a high-reflectance material and threading the inner surface of the light directing member 1.

With this feature, the bonding strength is improved by the threading and the illumination light is highly efficiently dispersed. That is, the illumination light is dispersed by breaking the total reflection condition of the illumination light directed through the light directing member 1 by the zigzag shape of the screw portion of the light directing member 1, and the illumination light is reflected at a high reflectance by the slanting surface of the screw thread portion of the lens barrel 2b or the mounting member 4. Moreover, the illumination of the subject is optimized by changing the screw configuration.

In all of the above-described embodiments, when the light directing member 1 is not thrown away after one use but is reused, it is preferable that the light directing member 1 be made of an optical plastic material with a glass transition temperature of at least 120° C. or higher. With this, disinfection after use is facilitated.

As described above with the present invention according to the first to seventh embodiments, since an easy-to-manufacture and inexpensive endoscope of a type being thrown away after one use or a type being thrown away after a limited number of uses and a method of manufacturing the same are provided by the above-mentioned workings, the industrial value of the present invention is great.

Further, according to the endoscope of the eighth to twelfth embodiments of the present invention, since both the illumination light from the front end surface of the light directing member and the illumination light from the light dispersing portion can be used and the light dispersing portion is integrally formed with the hollow cross section light directing member, the illumination distribution is made excellent with a simple arrangement and the cost is reduced.

Since the illumination light applied to the inside of the light directing member is again reflected toward the subject by providing the reflecting means inside the light directing member, the illumination light is effectively used.

What is claimed is:

1. An endoscope comprising an elongated insertion portion inserted into a subject, said insertion portion directing illumination light toward said subject and including an outer cylindrical light directing member being hard enough to maintain its configuration, an image sensing device provided inside said light directing member for converting light from said subject into an electric signal, and a circuit board electrically connected to said image sensing device and extending from said image sensing device to a rear end portion of said light directing member, said circuit board including electrodes formed at the rear end portion, and a signal cable and a light directing cable terminating at a connector, wherein said connector is provided to (a) connect to said electrodes for receiving said electric signal and (b) connect to said light directing member for transmitting the illumination light, and said connector simultaneously connects to or disconnects from both said electrodes and said light directing member.

2. An endoscope according to claim 1, wherein said connector includes an electric signal connection portion and a light directing connection portion and the electric signal connection portion is formed inside the light directing connection portion.

3. An endoscope according to claim 2, wherein said signal connection portion includes a plurality of contacts arranged in a direction of insertion of said circuit board for contacting said electrodes when said circuit board is inserted into the connector.

4. An endoscope according to claim 1, wherein said light directing member is made of a resin material.

5. An endoscope according to claim 3, wherein said insertion portion is connected to a light directing cable, and said connector is disconnectably connected to said light directing cable at a light direction connection portion.

6. An endoscope according to claim 5, wherein a light incident end of said light direction connection portion has substantially the same size and configuration as a light exit end of said light directing cable, wherein a light exit end of said light direction connection portion has substantially the same size and configuration as a light incident end of said light directing member, and wherein said light exit end of said light directing cable is connectable to add disconnectable from said light incident end of said light direction connection portion.

7. An endoscope according to claim 5, wherein a light incident end of said light direction connection portion has substantially the same size and configuration as a light exit end of said light directing cable, wherein a light exit end of said light direction connection portion has a configuration with a thickness the same as a wall thickness of a pipe of said light directing member, and wherein a light exit end of said light directing cable is connectable to and disconnectable from said light incident end of said light direction connection portion.

8. An endoscope according to claim 1, wherein said light directing member is made of an optical plastic material with a glass transition temperature of 120° C. or higher.

9. An endoscope according to claim 1, wherein said image sensing device includes an objective lens and a lens holder for holding said objective lens, wherein said objective lens is hermetically joined to said lens holder forming a first joint, and wherein said lens holder is hermetically joined to said light directing member forming a second joint.

10. An endoscope according to claim 9, wherein said first and second hermetic joints are realized by ultrasonic welding.

11. An endoscope according to claim 1, wherein a front end of said light directing member is hermetically sealed by an optical window.

12. An endoscope according to claim 11, wherein said optical window is made of the same material as said light directing member.

13. A method of manufacturing an endoscope in which an elongated insertion portion to be inserted into a subject directs illumination light for illuminating said subject, and comprises a cylindrical light directing member being hard enough to maintain its configuration, and an optical system and an image sensing device provided inside said light directing member for observing said subject, in which said image sensing device comprises a solid-state image sensing device for converting light from said optical system into an electric signal and a circuit board electrically connected to said solid-state image sensing device, in which said circuit board is formed to extend from said solid-state image sensing device to a rear end portion of said light directing member, and in which electrode portions for disconnectable electrical connection with a signal cable are formed at a rear end portion of said circuit board, wherein position adjustment of said optical system previously fixed to said front end portion of said light directing member, and said solid-state image sensing device is made by operating said rear end portion of said circuit board.

14. An endoscope comprising an elongated insertion portion inserted into a subject, said insertion portion including a light directing member of hollow cross section for directing illumination light for illuminating said subject, and an image sensing device provided inside said light directing member for observing said subject, and a light dispersing portion for dispersing said illumination light formed at a front end portion of said light directing member, wherein said light dispersing portion is formed on one of an outer surface and an inner surface of said light directing member and said light dispersing portion is one of a concentrical groove and a spiral groove.

15. An endoscope according to claim 14, wherein said light dispersing portion is formed on a front end side surface of said light directing member.

16. An endoscope according to claim 14, wherein said light dispersing portion is formed by decreasing an outside diameter of said light directing member toward a front end surface of said light directing member.

17. An endoscope comprising an elongated insertion portion inserted into a subject, said insertion portion including a light directing member of hollow cross section for directing illumination light for illuminating said subject, and an image sensing device provided inside said light directing member for observing said subject, a light dispersing portion for dispersing said illumination light formed at a front end portion of said light directing member, and reflecting means for reflecting outwardly said illumination light from said light directing member, wherein said reflecting means is provided on an inner surface of said light directing member.

18. An endoscope according to claim 17, wherein said reflecting means is a reflecting film.

19. An endoscope according to claim 18, wherein said reflecting film is an aluminum film.

20. An endoscope according to claim 17, wherein a structure for supporting said image sensing device is formed of a metal material of high reflectance and said structure provides said reflecting means.

21. An endoscope according to claim 20, wherein minute projections and depressions are formed on a surface of said structure.

22. An endoscope according to claim 21, wherein said structure is fixed to said light directing member by screws formed on an outer surface of said structure and on an inner surface of said light directing member.

23. An endoscope according to claim 17, wherein said light directing member is made of a transparent acrylic material.

24. An endoscope having a source of light for inserting into a subject, comprising an elongated, hollow outer light directing member having a front end for inserting into the subject, an elongated inner member disposed within said outer member, said inner member having
  a) an image sensing device for converting optical light from the subject into electric signals, said device disposed at the front end, and
  b) an electric circuit for processing said electrical signals disposed within said inner member;

said outer light directing member channeling light from the source to illuminate the subject, and a light dispersing portion disposed at the front end for dispersing the light to illuminate the subject, wherein said dispersing portion is one of a spiral groove and a concentric groove formed in said outer light directing member.

25. An endoscope according to claim 24 further comprising an optical window disposed at the front end and forming a transparent seal with said outer light directing member, and an objective lens disposed between said optical window and said image sensing device for transmitting light from the subject to the image sensing device.

* * * * *

UNITED STATES PATENT AND TRADEMARK OFFICE
CERTIFICATE OF CORRECTION

PATENT NO.     : 6,293,910 B1
DATED          : September 25, 2001
INVENTOR(S)    : Yamakita et al.

It is certified that error appears in the above-identified patent and that said Letters Patent is hereby corrected as shown below:

<u>Column 20,</u>
Line 24, "21" should be -- 20 --.

Signed and Sealed this

Twelfth Day of November, 2002

*Attest:*

*Attesting Officer*

JAMES E. ROGAN
*Director of the United States Patent and Trademark Office*